United States Patent
Lurie et al.

(10) Patent No.: US 6,587,726 B2
(45) Date of Patent: Jul. 1, 2003

(54) STIMULATORY DEVICE AND METHODS TO ELECTRICALLY STIMULATE THE PHRENIC NERVE

(75) Inventors: Keith G. Lurie, Minneapolis, MN (US); Todd M. Zielinski, Minneapolis, MN (US); Wolfgang Voelckel, Telfs (AT); Robert Patterson, Minneapolis, MN (US); Nemer Samniah, Haifa (IL); Scott McKnite, Minneapolis, MN (US); Karl Lindner, Natters (AT)

(73) Assignee: CPRx LLC, Eden Prairie, MN (US)

( * ) Notice: Subject to any disclaimer, the term of this patent is extended or adjusted under 35 U.S.C. 154(b) by 0 days.

(21) Appl. No.: 10/158,528

(22) Filed: May 29, 2002

(65) Prior Publication Data

US 2002/0188332 A1 Dec. 12, 2002

Related U.S. Application Data

(63) Continuation of application No. 09/533,880, filed on Mar. 22, 2000, now Pat. No. 6,463,327, which is a continuation-in-part of application No. 09/315,396, filed on May 20, 1999, now Pat. No. 6,312,399, which is a continuation-in-part of application No. 09/197,286, filed on Nov. 20, 1998, now Pat. No. 6,224,562, which is a continuation-in-part of application No. 09/095,916, filed on Jun. 11, 1998, now Pat. No. 6,234,985.

(51) Int. Cl.[7] .................................................. A61N 1/18
(52) U.S. Cl. .......................... 607/42; 128/898; 601/41
(58) Field of Search ............................... 607/2, 42, 48, 607/77; 601/15, 41; 128/206.24, 206.25, 898

(56) References Cited

U.S. PATENT DOCUMENTS

| 5,692,498 | A  | * | 12/1997 | Lurie et al. | ............. | 128/205.24 |
| 6,224,562 | B1 | * |  5/2001 | Lurie et al. | ..................... | 601/41 |
| 6,234,985 | B1 | * |  5/2001 | Lurie et al. | ..................... | 601/41 |
| 6,312,399 | B1 | * | 11/2001 | Lurie et al. | ..................... | 601/41 |
| 6,463,327 | B1 | * | 10/2002 | Lurie et al. | ..................... | 607/42 |

* cited by examiner

Primary Examiner—Jeffrey R. Jastrzab
(74) Attorney, Agent, or Firm—Townsend and Townsend and Crew LLP

(57) ABSTRACT

The invention provides exemplary devices and methods electrically stimulating the phrenic nerve. In one embodiment, electrodes are placed posterior and anterior in the region of the cervical vertebrae. Electrical current having a multi-phasic waveform is periodically applied to the electrodes to stimulate the phrenic nerve, thereby causing the diaphragm to contract.

5 Claims, 28 Drawing Sheets

STIMULATORY DEVICE AND METHODS TO ELECTRICALLY STIMULATE THE PHRENIC NERVE

CROSS-REFERENCES TO RELATED APPLICATIONS

This application is a continuation of U.S. patent application Ser. No. 09/533,880, filed Mar. 22, 2000 now U.S. Pat. No. 6,463,327 which is a continuation in part application of U.S. patent application Ser. No. 09/315,396, filed May 20, 1999 now U.S. Pat. No. 6,312,399, which is a continuation in part application of U.S. patent application Ser. No. 09/197,286, filed Nov. 20, 1998 now U.S. Pat. No. 6,224,562, which is a continuation in part application of U.S. patent application Ser. No. 09/095,916, filed Jun. 11, 1998 now U.S. Pat. No. 6,234,985, the complete disclosures of which are herein incorporated by reference.

BACKGROUND OF THE INVENTION

The invention relates generally to the field of cardiopulmonary resuscitation, artificial ventilation, treatment of various types of shock, and treatment of right ventricular failure. In particular, the present invention in some embodiments relates to devices and methods for increasing blood flow to the thorax, including increasing cardiopulmonary circulation during cardiopulmonary resuscitation procedures. In one aspect, increased blood flow to the thorax is accomplished by electrically stimulating the phrenic nerve. Stimulation of the phrenic nerve may also be used to ventilate a patient.

Worldwide, sudden cardiac arrest is a major cause of death and is the result of a variety of circumstances, including heart disease and significant trauma. In the event of a cardiac arrest, several measures have been deemed to be essential in order to improve a patient's chance of survival. These measures must be taken as soon as possible to at least partially restore the patient's respiration and blood circulation. One common technique, developed approximately 30 years ago, is an external chest compression technique generally referred to as cardiopulmonary resuscitation (CPR). CPR techniques have remained largely unchanged over the past two decades. With traditional CPR, pressure is applied to a patient's chest to increase intrathoracic pressure. An increase in intrathoracic pressure induces blood movement from the region of the heart and lungs towards the peripheral arteries. Such pressure partially restores the patient's circulation.

Traditional CPR is performed by active compression of the chest by direct application of an external pressure to the chest. This phase of CPR is typically referred to as the compression phase. After active compression, the chest is allowed to expand by its natural elasticity which causes expansion of the patient's chest wall. This phase is often referred to as the relaxation or decompression phase. Such expansion of the chest allows some blood to enter the cardiac chambers of the heart. The procedure as described, however, is insufficient to ventilate the patient. Consequently, conventional CPR also requires periodic ventilation of the patient. This is commonly accomplished by a mouth-to-mouth technique or by using positive pressure devices, such as a self-inflating bag which delivers air through a mask, an endotracheal tube, or other artificial airway.

In order to increase cardiopulmonary circulation induced by chest compression, a technique referred to as active compression-decompression (ACD) has been developed. According to ACD techniques, the active compression phase of traditional CPR is enhanced by pressing an applicator body against the patient's chest to compress the chest. Such an applicator body is able to distribute an applied force substantially evenly over a portion of the patient's chest. More importantly, however, the applicator body is sealed against the patient's chest so that it may be lifted to actively expand the patient's chest during the relaxation or decompression phase. The resultant negative intrathoracic pressure induces venous blood to flow into the heart and lungs from the peripheral venous vasculature of the patient. Devices and methods for performing ACD to the patient are described in U.S. Pat. Nos. 5,454,779 and 5,645,552, the complete disclosures of which are herein incorporated by reference.

Another successful technique for increasing cardiopulmonary circulation is by impeding air flow into a patient's lungs during the relaxation or decompression phase. By impeding the air flow during the relaxation or decompression phase, the magnitude and duration of negative intrathoracic pressure is increased. In this way, the amount of blood flow into the heart and lungs is increased. This creates a vacuum in the chest. As a result, cardiopulmonary circulation is increased. Devices and methods for impeding or occluding the patient's airway during the relaxation or decompression phase are described in U.S. Pat. Nos. 5,551,420 and 5,692,498 and co-pending U.S. application Ser. No. 08/950,702, filed Oct. 15, 1997. The complete disclosures of all these references are herein incorporated by reference.

The above techniques have proven to be extremely useful in enhancing traditional CPR procedures. As such, it would be desirable to provide still further techniques to enhance venous blood flow into the heart and lungs of a patient from the peripheral venous vasculature during both conventional and alternative CPR techniques. It would be particularly desirable to provide techniques which would enhance oxygenation and increase the total blood return to the chest during the relaxation or decompression phase of CPR.

In additional to CPR techniques, other situations exist where blood flow to the thorax is important. Hence, the invention is also related to techniques for returning blood to the thorax for other reasons, i.e., for treating various types of shock, right ventricular failure, post resuscitation pulseless electrical activity, and the like. The invention is also related to providing novel techniques to ventilate a patient, especially in cases where intubation is undesirable or where ventilation can result in the bursting of pulmonary alveoli and bronchioles.

SUMMARY OF THE INVENTION

In certain embodiments, the invention provides methods and devices for increasing cardiopulmonary circulation when performing cardiopulmonary resuscitation. The methods and devices may be used in connection with most generally accepted CPR methods. In one exemplary method, a patient's chest is actively compressed during the compression phase of CPR. At least some of the respiratory muscles, and particularly the inspiratory muscles, are then stimulated to contract during the relaxation or decompression phase to increase the magnitude and prolong the duration of negative intrathoracic pressure during the relaxation or decompression phase, i.e., respiratory muscle stimulation increases the duration and degree that the intrathoracic pressure is below or negative with respect to the pressure in the peripheral venous vasculature. By enhancing the amount of venous blood flow to the heart and lungs, cardiopulmonary circulation is increased.

Among the respiratory muscles that may be stimulated to contract are the diaphragm and the chest wall muscles, including the intercostal muscles. The respiratory muscles may be stimulated to contract in a variety of ways. For example, the diaphragm may be stimulated to contract by supplying electrical current or a magnetic field to various nerves or muscle bundles which when stimulated cause the diaphragm to contract. Similar techniques may be used to stimulate the chest wall muscles to contract. A variety of pulse trains, pulse widths, pulse frequencies and pulse waveforms may be used for stimulation. Further, the electrode location and timing of pulse delivery may be varied. In one particular aspect, an electrical current gradient or a magnetic field is provided to directly or indirectly stimulate the phrenic nerve.

To electrically stimulate the inspiratory motor nerves, electrodes are preferably placed on the lateral surface of the neck over the point where the phrenic nerve, on the chest surface just lateral to the lower sternum to deliver current to the phrenic nerves just as they enter the diaphragm, on the upper chest just anterior to the axillae to stimulate the thoracic nerves, in the oral pharyngeal region of the throat, or on the larynx itself. However, it will be appreciated that other electrode sites may be employed. For example, in one embodiment the respiratory muscles are stimulated by a transcutaneous electrical impulse delivered along the lower antero-lat margin of the rib cage. In one embodiment, inspiration is induced by stimulating inspiratory muscles using one or more electrodes attached to an endotracheal tube or pharyngeal tube.

A variety of other techniques may be applied to further enhance the amount of venous blood flow into the heart and lungs during the chest relaxation or decompression phase of CPR. For example, the chest may be actively lifted during the relaxation or decompression phase to increase the amount and extent of negative intrathoracic pressure. Alternatively, the chest may be compressed by a circumferential binder. Upon release, the chest recoil enhances venous return. During interposed counterpulsation CPR, pressing on the abdomen in an alternating fashion with chest compression also enhances blood return to the heart. In another technique, air flow to the lungs may be periodically occluded during at least a portion of the relaxation or decompression phase. Such occlusion may be accomplished by placing an impedance valve into the patient's airway, with the impedance valve being set to open after experiencing a predetermined threshold negative intrathoracic pressure.

In one particular aspect of the method, respiratory gases are periodically supplied to the patient's lungs to ventilate the patient. In another aspect, a metronome is provided to assist the rescuer in performing regular chest compressions.

In still another aspect, the respiratory muscles are stimulated only during certain relaxation or decompression phases, such as every second or third relaxation or decompression phase. In yet another aspect, a defibrillation shock is periodically delivered to the patient to shock the heart or an electrical impulse is delivered to periodically initiate transthoracic pacing.

The invention further provides an exemplary device to assist in the performance of a cardiopulmonary resuscitation procedure. The device comprises a compression member which is preferably placed over the sternum and manually or mechanically pressed to compress the chest. At least one electrode is coupled to the compression member in a way such that the electrode will be positioned to supply electrical stimulation to the respiratory muscles to cause the respiratory muscles to contract following compression of the chest.

In one preferable aspect, a pair of arms extend from the compression member, with one or more electrodes being coupled to the end of each arm. Preferably, the arms are fashioned so as to be adapted to be received over the lower rib cage when the compression member is over the sternum. In this way, the electrodes are placed in a preferred location to stimulate the respiratory muscles to contract. Conveniently, the arms may be fashioned of a flexible fabric so that the arms will conform to the shape of the chest, thereby facilitating proper placement of the electrodes. In one preferable aspect, the electrodes comprise adhesive electrically active pads.

In one particular aspect, a voltage controller or a potentiometer is provided to control the stimulation voltage delivered to the electrode. In this way, a rescuer or a closed loop feedback system may change the voltage output of the electrode to ensure adequate respiratory muscle stimulation. A metronome may optionally be provided and incorporated into the device to assist a rescuer in performing regular chest compressions with the compression member. In another aspect, the stimulation sites may be varied on a periodic basis with an automatic switching box to avoid respiratory muscle or chest wall muscle fatigue.

In one particularly preferable aspect, a pressure or force sensor is disposed in the compression member to sense when a compressive force is being applied to the compression member. Control circuitry may also provided to cause actuation of the electrode when the sensor senses an external compression that is being applied to the compressive member. In this way, a sensor-directed electrical impulse may be emitted from the electrode to transcutaneously stimulate the respiratory muscles to contract at the end of the compression phase. Endotracheal stimulation of respiration muscles is also possible in a similar manner. In cases where a significant delay occurs between delivery of the stimulant and full respiratory muscle contraction, the sensor may be employed to sense when mid-compression (or some other point in the compression phase) occurs to initiate respiratory muscle stimulation sometime before the start of the relaxation or decompression phase.

In still another aspect, a power source is coupled to the electrode. The power source may be integrally formed within the device or may be a separate power source which is coupled to the electrode. As another alternative, the electrode may be coupled to a defibrillator to provide a defibrillation shock or to initiate trans-thoracic cardiac pacing. In another aspect, the voltage controller and power source may be part of a sensor-compression-stimulation device or coupled to the device but separated from the compression-sensor-stimulation device. In still another alternative, the device may be coupled to a ventilator to periodically ventilate the patient based on the number of compressions. In another aspect, impedance or electrical impulses generated by chest compression may be sensed and used by a remote power source and pacer-defibrillation unit to stimulate respiratory muscle contraction using the same sensing electrode(s) or other means to also stimulate the respiratory muscles to contract.

The invention further provides an exemplary device to assist in the performance of cardiopulmonary resuscitation by stimulating the phrenic nerve to cause the diaphragm and/or other respiratory muscles to contract during the relaxation or decompression phase of CPR. Such stimulation may be accomplished by delivering either electrical or magnetic energy to the phrenic nerve. In one embodiment, the phrenic nerve stimulators may be coupled to a chest compression sensor to coordinate chest compressions with the electric or magnetic stimulation of the phrenic nerve. In another aspect, a signal, such as an audible signal or blinking light, may be produced each time electrical inspiration occurs, and manual chest compression is timed based on the emitted signal.

In another embodiment, the device comprises a ventilation member which is coupled to the patient's airway to assist in the flow of respiratory gases into the patient's lungs. A sensor may be coupled to the ventilation member to induce application of an electrical current to the phrenic nerve to cause the diaphragm or other respiratory muscles to contract. In this way, a ventilation member which is typically employed to provide ventilation to a patient during a CPR procedure may also function as a stimulant to cause contraction of the diaphragm or other respiratory muscles during the relaxation or decompression phase of CPR. In this manner, the amount of venous blood flowing to the heart and lungs will be enhanced.

A variety of ventilation members may be employed, including endotracheal tubes, laryngeal mask airways, or other ventilation devices which are placed within the larynx, esophagus, or trachea. In one particularly preferable aspect, a pair of electrodes is coupled to the ventilation member so that the device may operate in a unipolar or multipolar manner to stimulate the phrenic nerve. Other aspects include transcutaneous phrenic nerve stimulation with a collar-like device placed around the neck which includes one or more electrodes located on both anterior and posterior surfaces to stimulate the phrenic nerve.

In another embodiment, a system is provided to produce a cough. The system comprises at least one electrode that is adapted to be positioned on a patient to stimulate the abdominal muscles to contract. A valve is also provided and has an open position and a closed position. A controller is coupled to the electrode and the valve and is configured to open the valve after the electrode is actuated to cause the patient to cough,. i.e. the valve allows pressure to build, then opens to release pressure and enhance expiratory gas flow rate similar to a cough. In one aspect, the controller is configured to open the valve for a time in the range from about 10 ms to about 500 ms after the abdominal muscles are stimulated to contract.

The invention further provides an exemplary method for increasing cardiopulmonary circulation when performing cardiopulmonary resuscitation on a patient in cardiac arrest. According to the method, at least some of the abdominal muscles are periodically stimulated to contract sufficient to enhance the amount of venous blood flow into the heart and lungs. In one aspect, the abdominal muscles may be electrically stimulated to contract while preventing respiratory gases from exiting the lungs, and then permitting respiratory gases from exiting the lungs to produce a cough. In another aspect, the patient's chest is actively compressed during a compression phase and the patient's chest is permitted to rise during a decompression phase. Further, the abdominal muscles are stimulated to contract during a time period which ranges between a latter portion of the decompression phase to a mid portion of the compression phase.

In another embodiment, a method is provided for increasing blood flow to the thorax of a patient. According to the method, the phrenic nerve is periodically stimulated to cause the diaphragm to contract and thereby causing an increase in the magnitude and duration of negative intrathoracic pressure. This results in a "gasp" creating a vacuum, thereby sucking more air and blood into the thorax. Further, when airflow is periodically occluded from flowing to the lungs during contraction of the diaphragm with a valve that is positioned to control airflow into the patient's airway, the magnitude and duration of negative intrathoracic pressure is further increased to force more blood into the thorax.

In one particular aspect, the phrenic nerve is stimulated by applying electrical current to the phrenic nerve with electrodes that are positioned over the cervical vertebrae between C3 and C7. More preferably, the electrodes are placed both posterior and anterior between C3 and C5. In another aspect, the electrical current is provided in multiphasic form. For example, the wave form may be biphasic, including asymmetrical biphasic. Depending on the particular treatment, the electrical signal may be within certain current ranges, certain frequency ranges, and certain pulse width ranges. Merely by way of example, biphasic electrical current may be used that is in the range from about 100 milliamps to about 2,000 milliamps at a frequency in the range from about 10 Hz to about 100 Hz, and in pulse widths in the range from about 1 μs to about 5 ms.

The methods of the invention may also be used to treat a wide variety of conditions, including for example, hemorrhagic shock, hypovolemic shock, cardiogenic shock, post resuscitation pulseless electrical activity, right ventricular failure, and the like. For instance, when the patient is suffering from hemorrhagic shock, the phrenic nerve may be stimulated about 5 to about 30 times per minute. Further, the phrenic nerve may be stimulated after each breath for time intervals of about 0.25 seconds to about 5 seconds, or in the range from about twice per every one breath to about once about every five breaths. For hypovolemic shock, the phrenic nerve may be stimulated about 5 to about 40 times per minute. When suffering from cardiogenic shock, the phrenic nerve may be stimulated about 5 to about 80 times per minute.

In some cases, the patient may be suffering from cardiac arrest, and the phrenic nerve may be stimulated about 10 to about 100 times per minute in combination with chest compressions that are performed at a rate in the range from about 50 compressions to about 100 compressions per minute. In one option, the chest compressions may be sensed and used to control the timing of phrenic nerve stimulations. Alternatively, a repeating audio and/or visual signal may be provided to indicate to a rescuer when to perform the chest compressions based on the timing of phrenic nerve stimulation. Such a process is described in greater detail in copending U.S. patent application Ser. No. 09/532,601, filed on the same date as the present application, the complete disclosure of which is herein incorporated by reference. In another option, the number of chest compressions relative to the number of phrenic nerve stimulations may be counted.

For patients suffering from post resuscitation pulseless electrical activity, the phrenic nerve may be stimulated about 5 to about 60 times per minute. When suffering from right ventricular failure, the phrenic nerve may be stimulated about 5 to about 80 times per minute. The duration of the stimulation may last from 0.25 to about 6 seconds.

In another embodiment, a method is provided for ventilating a patient, such as when the patient is suffering from respiratory distress or apnea. According to the method, electrodes are placed posterior and anterior on the cervical vertebrae, such as in the C3 to C5 region. Electrical current having a multiphasic waveform, such as an asymmetric biphasic waveform, is supplied to the electrodes to stimulate the phrenic nerve, thereby causing the diaphragm to contract and draw respiratory gases into the patient's lungs. Conveniently, the phrenic nerve may be stimulated about 3 to about 30 times per minute.

In still another embodiment, a method is provided for increasing blood flow to the thorax of a patient by repeatedly electrically stimulating the diaphragm to contract with at least two electrodes. The magnitude of negative intrathoracic pressure is sensed after diaphragmatic stimulation, and the amount of current that is supplied to the electrode is controlled based on the measured pressure. For example, the sensed measurement may be used to continually adjust the current level so that the magnitude of negative intrathoracic pressure is within the range from about −5 mmHg to about −30 mmHg during diaphragmatic stimulation.

In another embodiment, a stimulation device is provided that comprises a generally flat back plate that is configured to be placed below a patient's back when the patient is lying down. A neck support is coupled to the back plate and serves to tilt the patient's head backward. Further, at least two electrodes are coupled to the stimulation device to electrically stimulate the patient. For example, the electrodes may be employed to electrically stimulate the phrenic nerve in a manner similar to other embodiments described herein. Optionally, a pair of defibrillation electrodes may also be coupled to the stimulation device to permit a defibrillating shock to be applied.

DESCRIPTION OF THE SPECIFIC EMBODIMENTS

Figure 1:
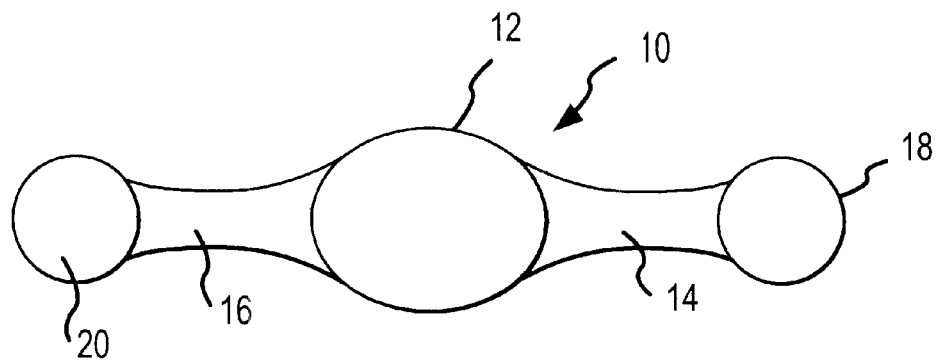
FIG. 1 is a top plan view of an exemplary respiratory muscle stimulation device according to the invention.

The present invention in certain embodiments provides methods and devices for increasing cardiopulmonary circulation when performing cardiopulmonary resuscitation. As is known in the art, cardiopulmonary resuscitation techniques involve a compression phase where the chest is compressed and a relaxation or decompression phase where the chest is allowed to return to its normal position. The methods and devices of the invention may be used in connection with any method of CPR in which intrathoracic pressures are intentionally manipulated to improve cardiopulmonary circulation. For instance, the present invention may be used in connection with standard, manual, closed-chest CPR, interposed abdominal counterpulsation CPR, with a mechanical resuscitator, such as the Michigan Instruments "Thumper", with ACD-CPR, with "Lifestick" CPR, and the like. In addition, certain embodiments may be used to induce inspiration and/or coughing. This may help to maintain blood pressure during cardiac arrest and may help patients that are incapable of voluntary inspiration or coughing.

In a broad sense, one aspect of the present invention provides for stimulating contraction of at least some of the respiratory muscles during the relaxation or decompression phase of CPR to enhance and sustain the duration of negative intrathoracic pressure during the relaxation or decompression phase. The significance of the increase in negative intrathoracic pressure during the relaxation or decompression phase is that more venous blood is forced into the chest from the peripheral venous vasculature. As a result, more blood is allowed to be oxygenated and more blood is forced out of the chest during the next compression. Upon contraction of the respiratory muscles, the patient will typically "gasp". The invention thus provides techniques for consistently inducing a "gasp" after chest compression.

The decrease in intrathoracic pressure produced by electrical stimulation of the inspiratory muscles, including the diaphragm, during the chest relaxation phase of CPR is associated with an increase in coronary perfusion pressure and thus an increase in blood flow to the heart. The coronary perfusion pressure to the heart during the decompression phase can be calculated by the mathematical difference between the aortic and right atrial pressure. Right atrial pressure is lowered by inspiratory effort, and therefor the aortic-right atrial gradient or the coronary perfusion pressure is increased by stimulation of inspiratory effort.

The respiratory muscles that may be stimulated to contract to enhance ventilation and/or to alter intrathoracic pressures include the diaphragm, the chest wall muscles, including the intercostal muscles and the abdominal muscles. Specific chest wall muscles that may be stimulated to contract include those that elevate the upper ribs, including the scaleni and sternocleidomastoid muscles, those that act to fix the shoulder girdle, including the trapezii, rhomboidei, and levatores angulorum scapulorum muscles, and those that act to elevate the ribs, including the serrati antici majores, and the pectorales majores and minores as described generally in Leslie A. Geddes, "Electroventilation—A Missed Opportunity?", Biomedical Instrumentation & Technology, July/August 1998, pp. 401–414, the complete disclosure of which is herein incorporated by reference. Of the respiratory muscles, the two hemidiaphragms and intercostal muscles appear to be the greatest contributors to inspiration and expiration.

The invention provides a variety of ways to stimulate respiratory muscle contraction so that the magnitude and extent of negative intrathoracic pressure during the relaxation or decompression phase may be increased. Preferably, the respiratory muscles are stimulated to contract by transcutaneous or transtracheal electrical field stimulation techniques. For example, to stimulate the diaphragm, the phrenic nerve may be stimulated in the neck region near C3–C7, such as between C3, C4 or C5, or where the phrenic nerves enter the diaphragm. Alternative techniques for stimulating diaphragmatic contraction include magnetic field stimulation of the diaphragm or the phrenic nerve. Magnetic field stimulation may also be employed to stimulate the chest wall muscles. Electrical field stimulation of the diaphragm or the chest wall muscles may be accomplished by placing one or more electrodes on the skin, preferably in the vicinity of the neck or the lower rib cage (although other locations may be employed) and then providing an electrical voltage gradient between electrodes that induces transcutaneous current flow to stimulate the respiratory muscles to contract. Still further, subcutaneous electrodes may also be used to stimulate respiratory muscle contraction.

In another broad aspect of the invention, venous return may be enhanced by compressing the abdomen. For example, downward compression provided to the abdomen causes the diaphragm to move upward into the thoracic cavity. As the abdomen is compressed, venous blood is physically forced out of the abdominal cavity and into the thoracic cavity. Advantageously, when the abdomen is compressed, there is an increase in resistance to the flow of blood from the thoracic aorta into the abdominal aorta. This gradient causes a greater proportion of arterial blood flowing to the brain and to the heart. In one aspect, abdominal compression may start during the second half of the decompression phase and last until the compression phase or about half way through the compression phase. The use of abdominal compression during CPR is described generally in J. M. Christenson, et. al., "Abdominal Compressions During CPR: Hemodynamic Effects of Altering Timing and Force", The Journal of Emergency Medicine, Vol 10, pp 257–266, 1992, the complete disclosure of which is herein incorporated by reference.

According to the invention, one way to contract the abdominal muscles is by electrical stimulation. For example, one or more electrodes may be positioned on the abdominal area at a variety of locations, including the back. Hence, the abdominal muscles may be made to contract at specific time intervals in relation to chest compression and/or inspiratory muscle electrical stimulation. As the abdominal muscles are electrically stimulated, the abdominal cavity squeezes to force the diaphragm upward into the thoracic cavity. Also, venous blood is moved from the abdomen to the thorax, and right atrial pressure increases. In this manner, venous blood is actively transported to the thorax. Further, when abdominal compression extends into the compression phase of CPR, exhalation is transformed from a passive to a more active process. Further, an increase in coronary perfusion pressure is obtained.

The techniques employed to stimulate the inspiratory muscles and/or nerves and to stimulate the abdominal muscles may be utilized either alone or in combination. These stimulation techniques may also be used with or without active chest compression. For example, even in the absence of active chest compression, large swings in intrathoracic pressure induced by electrical stimulation of the inspiratory muscles and/or nerves either alone or concomitantly with abdominal musculature stimulation will enhance vital organ perfusion and increase the chances for resuscitation.

The inspiratory muscles and/or nerves are preferably stimulated to contract immediately after the chest is compressed. Preferably, the inspiratory muscles and/or nerves are stimulated in a manner such that as soon as the compression phase is over, the intrathoracic pressure falls secondary to electrical stimulation of the inspiratory muscles. The compression phase may be configured to last approximately 50% of the CPR cycle. However, in some cases it may be desirable to shorten the compression phase and lengthen the decompression phase to further enhance venous return.

Abdominal compression and/or abdominal musculature stimulation may occur mid-way through the decompression phase and continue through at least the beginning of the compression phase. As previously described, at the end of the compression phase, intrathoracic pressure is lowered to enhance venous blood return. This may be augmented by causing the respiratory muscles, including the diaphragm, to contract. As the abdomen is compressed or the abdominal muscles are stimulated to contract mid-way through the decompression phase, the diaphragms are pushed actively upward into the thorax to force respiratory gases out of the chest and venous blood is forced into the thorax. When the compression phase is reached and the abdomen is still contracted, there is an increase in resistance to the flow of blood from the thoracic aorta into the abdominal aorta. This gradient causes a greater proportion of arterial blood flowing to the brain and to the heart.

In one aspect of the invention, the abdominal muscles may be stimulated sequentially in a valve-like manner so as to squeeze venous blood out of an area. For example, two electrodes may be spaced-apart from each other to form an electrode pair. Multiple pairs may be positioned lengthwise on the patient. The pairs of electrodes may be sequentially actuated, beginning from a bottom pair, to force blood out of the abdominal area into the thoracic cavity. Alternating the pattern in which the electrodes are actuated may help to prevent muscle fatigue.

The respiratory and abdominal muscle stimulation techniques of the invention may be used in connection with or in close association with various other techniques designed to treat or diagnose the patient receiving CPR. For example, during the relaxation or decompression phase, the patient's airway may be occluded to prevent foreign (outside) air or respiratory gases from flowing to the patient's lungs. In this way, the magnitude and duration of negative intrathoracic pressure during the relaxation or decompression phase are further enhanced. Exemplary devices and methods for occluding the patient's airway during the relaxation or decompression phase are described in U.S. Pat. Nos. 5,551,420 and 5,692,498 and co-pending U.S. application Ser. No. 08/950,702, previously incorporated herein by reference. As another example, the respiratory muscle stimulation techniques of the invention may be used in connection with ACD-CPR where the patient's chest is actively lifted during the relaxation or decompression phase to further enhance and sustain the duration of negative intrathoracic pressure during the relaxation or decompression phase.

The electrodes employed by the invention to stimulate respiratory muscle contraction may optionally be coupled to a defibrillator to deliver a defibrillation shock to the heart, or to supply energy to initiate transthoracic or transhacheal cardiac pacing. Since the device is preferably in contact with the skin, the device may optionally include various sensors to monitor various physiological parameters. For example, the device may include oxygen sensors, temperature sensors, or sensors to monitor $O_2$ saturation. Further, sensors may be provided to sense surface cardiac electrograms. The device may also be employed to deliver drugs transcutaneously.

In one embodiment, an adhesive compressive pad is placed over the lower portion of the sternum. Compressions are applied as with standard manual CPR to a depth of about two to three inches. A sensor is incorporated in a compression region of the pad and is employed to signal the triggering of respiratory muscle contraction. Preferably, portions of the compressive pad are electrically active to stimulate diaphragmatic and/or chest wall muscle contraction upon receipt of a signal from the sensor. In one aspect, the stimulator may emit a signal, such as an audible signal, a visual signal or the like, allowing the rescuer to time chest compressions based on the emitted signal.

The invention also provides techniques for increasing blood flow to the thorax for non-CPR applications. For example, in certain embodiments, the invention provides for stimulation of the phrenic nerve at the cervical vertebrae to cause diaphragmatic contraction, thereby increasing the magnitude and duration of negative intrathoracic pressure. To further increase the magnitude and duration of negative intrathoracic pressure, a valve is employed to prevent the flow of respiratory gases to the lungs during at least a portion of the time when the diaphragm is contracting. Examples of such valves are described in U.S. Pat. Nos. 5,551,420 and 5,692,498 and co-pending U.S. application Ser. No. 08/950,702, previously incorporated herein by reference. Such techniques are particularly useful when treating patients suffering from hemorrhagic shock, hypovolemic shock, cardiogenic shock, post resuscitation pulseless electrical activity, right ventricular failure, and the like. Merely by way of example, the phrenic nerve may be stimulated as follows: for hemorrhagic shock, about 5 to about 30 times per minute; for hypovolemic shock, about 5 to about 30 times per minute; for cardiogenic shock, about 5 to about 80 times per minute; for pulseless electrical activity, about 5 to about 60 times per minute. Typically, the valve will be controlled so that respiratory gases are prevented from reaching the lungs as the diaphragm begins to contract so that the negative intrathoracic pressure will reach at least −5 mmHg to about −30 mmHg. At this time, the valve may be opened to permit gases to reach the lungs. Further, a sensor may be employed to sense the pressure within the thorax. A feedback signal from the sensor may then be employed to control the electrical signal sent to the electrodes so that the negative intrathoracic pressure may be maintained at optimal levels.

The techniques employed to increase the return of blood to the thorax may find particular use when treating patients suffering shock due to gunshot wounds, and may also be used for patients who suffer from a severe myocardial infarction and shock. Presently available drugs are unable to provide such a function.

Phrenic nerve stimulation may also be used to electrically ventilate a patient. Such a process is particularly useful in applications where intubation is undesirable or when positive pressure ventilation can cause difficulties with bursting of pulmonary alveoli and bronchioles.

One way to stimulate the phrenic nerve (for each of the applications described above) is with the use of one or more electrodes that are placed on the patient's neck, preferably at the C3 to C7 region of the cervical vertebrae, and more preferably at the C3 to C5 region. In one aspect, the electrode may be placed both anterior and posterior. Further, a multiphase wave form, such as a biphasic waveform, including asymmetrical biphasic waveforms, may be employed. Such a configuration is particularly useful in reducing the amount of power required, reducing muscle fatigue, and increasing tidal volume (during ventilation).

Depending on the particular treatment, the electrical signal may have a wide range of currents, a wide range of frequencies, and a wide range of pulse widths. Merely by way of example, electrical current may be used that is in the range from about 100 milliamps to about 2,000 milliamps at a frequency in the range from about 10 Hz to about 100 Hz, and in pulse widths in the range from about 1 μs to about 5 ms.

Figure 2:
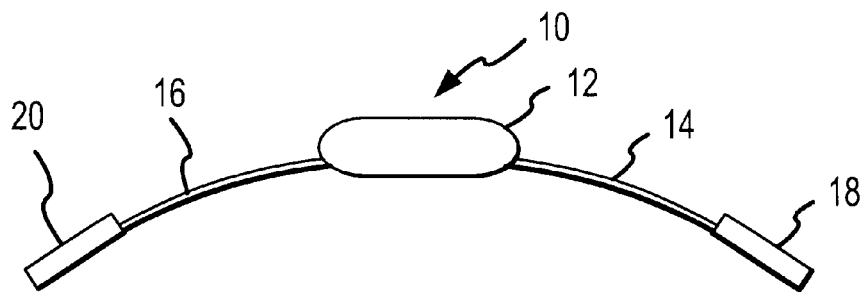
FIG. 2 is a side view of the device of FIG. 1.
Figure 3:
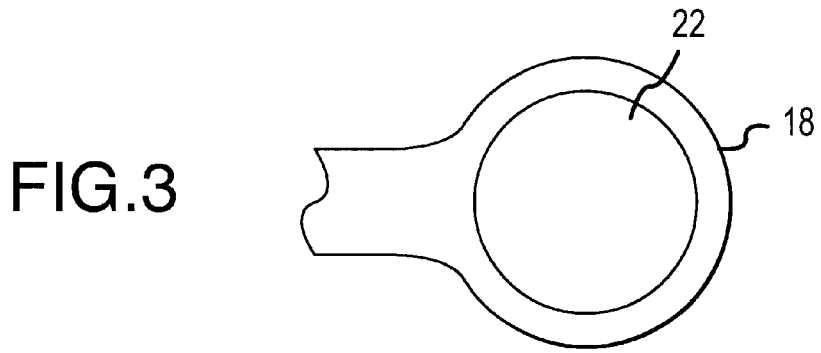
FIG. 3 is a detailed bottom view of an end member of the device of FIG. 1 showing an electrode for stimulating the respiratory muscles.

Referring now to FIGS. 1 and 2, an exemplary embodiment of a device 10 to provide respiratory muscle contraction during the performance of CPR will be described. Device 10 comprises a compression member 12 which is configured so that it may be received over the patient's chest in the area of the sternum. In this way, compression member 12 may be pressed downward to compress the patient's chest during the compression phase of CPR. Coupled to compression member 12 by a pair of arms 14 and 16 are a pair of end elements 18 and 20, respectively. As best shown in FIG. 3, end element 18 includes an electrode 22 on a bottom surface, it being appreciated that end element 20 or compression member 12 may include a similar electrode. Electrode 22 may comprise an adhesive electrically active pad, such as an R2 pad, commercially available from 3M. Electrodes 22 may also include a conductive gel. Other electrodes that may be employed include electrodes constructed of stainless steel, carbon-filled silicone rubber, platinum, iridium, silver silver-chloride, and the like. The electrode may be applied to the skin surface or may pierce the skin surface. It will also be appreciated that electrode 22 may be configured to operate in a monopolar manner, a bipolar manner or a multipolar manner. Further, electrode 22 may be configured to deliver electrical stimulation at different frequencies, pulse widths, pulse trains and voltage outputs to optimize respiratory muscle stimulation. The configuration of arms 14 may be varied to vary the lead vector produced by electrode 22. For example, the lead vector may be from one side of the chest to the other, to the midcompression region, or from one lead to the other on the same side of the chest. Device 10 may also be configured to deliver an output based, at least in part, upon the chest wall impedance. An energy source is coupled to the electrodes to deliver low energies, e.g., less than about 2 amps, to stimulate the respiratory muscles.

Although electrodes 22 have been described as electrodes which provide electrical stimulation, it will be appreciated that device 10 can be modified to provide a magnetic field to stimulate the respiratory muscles to contract. For example, a magnetic field may be applied to the phrenic nerve to produce diaphragmatic and/or chest wall muscle stimulation. As such, an upper back pad may be needed for optimal phrenic nerve stimulation.

Exemplary techniques for stimulating the respiratory muscles, and particularly the diaphragm, to contract, including techniques for providing both electrical and magnetic stimulation of the inspiratory motor nerves, are described in L. A. Geddes, "Electrically Produced Artificial Ventilation," Medical Instrumentation 22(5): 263–271 (1988); William W. L. Glenn et al., "Twenty Years of Experience in Phrenic Nerve Stimulation to Pace the Diaphragm," Pace 9:780–784 (November/December 1986, Part 1); P. L. Kotze et al., "Diaphragm Pacing in the Treatment of Ventilatory Failure," Sant. Deel 68:223–224 (Aug. 17, 1995); L. A. Geddes et al., "Inspiration Produced by Bilateral Electromagnetic, Cervical Phrenic Nerve Stimulation in Man," IEEE Transactions on Biomedical Engineering 38(9):1047–1048 (October 1991); L. A. Geddes et al., "Optimum Stimulus Frequency for Contracting the Inspiratory Muscles with Chest-Surface Electrodes to Produce Artificial Respiration," Annals of Biomedical Engineering 18:103–108 (1990); Franco Laghi et al., "Comparison of Magnetic and Electrical Phrenic Nerve Stimulation in Assessment of Diaphragmatic Contractility," American Physiological Society, pp. 1731–1742 (1996); and William W. L. Glenn et al., "Diaphragm Pacing by Electrical Stimulation of the Phrenic Nerve," Neurosurgery 17(6):974–984 (1985). The complete disclosures of all these references are herein incorporated by reference in their entirety. The electrodes of the invention may be configured to operate in a monopolar manner, a bipolar manner, or a multi-polar manner.

Arms 14 and 16 are preferably constructed of a flexible material, including fabrics, such as a nylon fabric, elastomeric materials, including rubbers, plastics and the like, to facilitate proper placement of electrodes 20 on the patient. Optionally; arms 14 and 16 may be pivotally attached to compression member 12 to allow electrodes 20 to be placed at a variety of locations on the patient.

Figure 4:
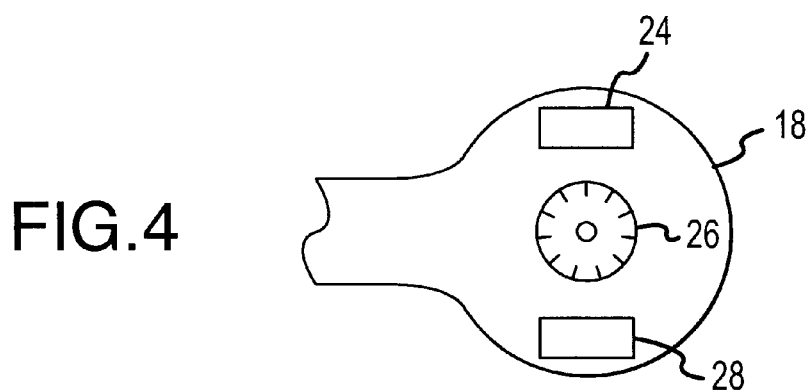
FIG. 4 illustrates a top view of the end member of FIG. 3 showing a potentiometer, a metronome, and a power source.

As illustrated in FIG. 4, a top side of end element 18 includes a metronome 24. Metronome 24 assists the rescuer in performing regular chest compressions when performing CPR by emitting regular audible or visual signals. This, in turn, aids in the coordinated timing between the compression of the chest and the stimulation of the respiratory muscles during the relaxation or decompression phase. End element 18 further includes a voltage controlling mechanism, such as a potentiometer 26, which enables the rescuer to change the voltage output of electrode 22 (see FIG. 3) to ensure adequate diaphragmatic stimulation. In one alternative, proper voltage may be determined automatically depending upon chest wall impedance that is measured with a impedance meter. In this way, device 10 may be configured so that it does not over stimulate or under stimulate the inspiratory motor nerves. End element 18 still further includes an energy source 28 which provides energy to the various electrical components, sensors, impedance meters, electrodes, and the like of device 10. Energy source 28 may conveniently comprise a battery that is stored within end element 18. Alternatively, a wide variety of external energy sources may be employed to operate device 10. For example, electrical energy may be provided by a ventilator which is employed to ventilate the patient, a defibrillator which may optionally be employed to provide defibrillation and transthoracic cardiac pacing and house the electrical components of a sensing system, an electrical generator which converts mechanical energy provided by the rescuer during compression of compression member 12 to electrical energy, and the like.

Although not shown, device 10 may optionally include a variety of displays, instructions for use, and controls that may be located on compression member 12, arms 14 or end elements 18. For example, device 10 may include a force, pressure or depth display which displays the amount of force, pressure or depth being applied to compression member 12 by the rescuer. In this way, the rescuer may be provided with information regarding the amount of force being supplied to compression member 12. Preferred force ranges may be included on device 10 so that the rescuer may determine if he is within a recommended force range. Device 10 may also include a compression counter display which displays the number of compressions experienced by compression member 12. The compression counter may be configured to display cycles of compressions to allow the rescuer to visualize the number of compressions that are performed for every respiratory muscle stimulation. Device 10 may still further include a surface electrogram sensing display to display information relating to a surface electrogram. Still further, a physiological parameter display may be provided to display various physiological parameters such as $O_2$ saturation, $CO_2$ saturation, skin temperature, and the like.

Figure 5:
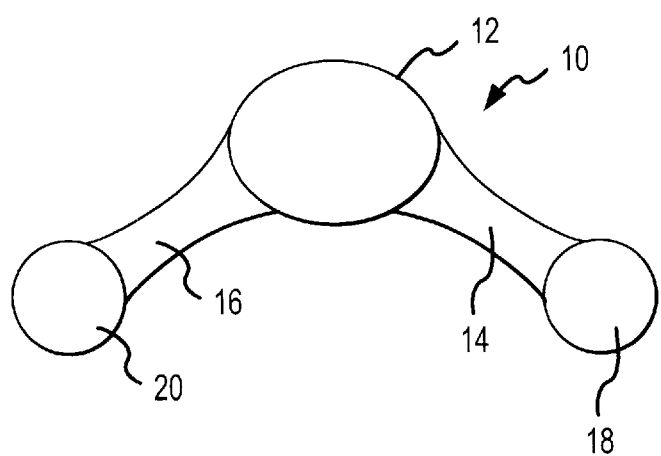
FIG. 5 is a top plan view of an alternative embodiment of a respiratory muscle stimulation device according to the invention.

As shown in FIG. 5, device 10 may be provided with a wishbone configuration so that end elements 18 are placed over the lower margin of the rib cage. Arms 14 and 16 may be configured to be fixedly mounted relative to compression member 12 so that the electrodes will always be placed at about the same region on the chest. Alternatively, arms 14 and 16 may be movably mounted to compression member 12 so that the position of the electrodes on the patient may be adjusted. As previously described, arms 14 and 16 may be configured to be constructed of either a flexible or a rigid material to facilitate proper placement of the electrodes on the patient.

Figure 5A:
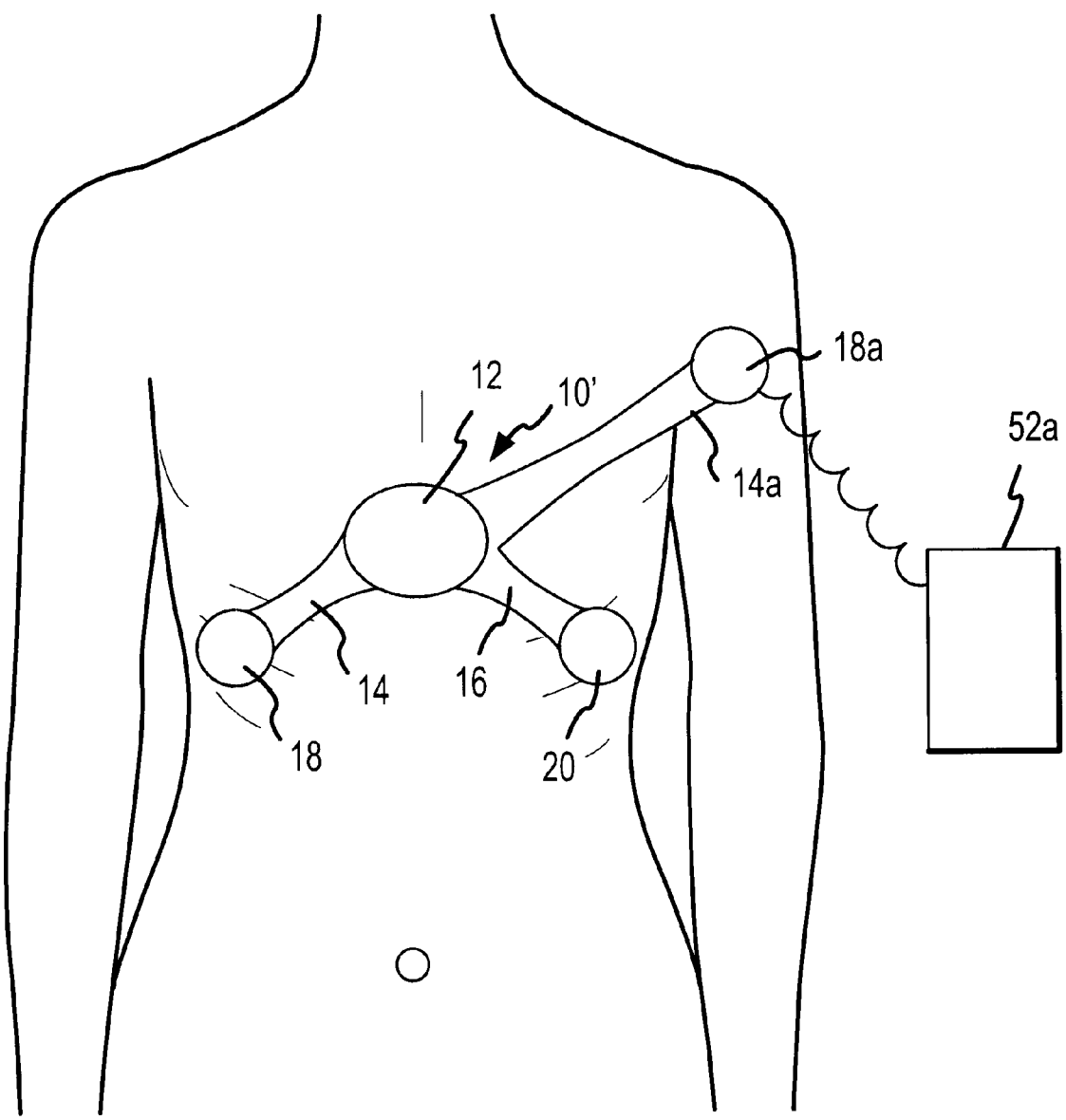
FIG. 5A illustrates yet another alternative embodiment of a respiratory muscle stimulation device according to the invention.

In another embodiment illustrated in FIG. 5A, a device 10' is provided which is similar to device 10 of FIG. 5 (with similar elements being labeled with the same reference numerals) and further includes an arm 14a having an end element 18a which is placed over the left axilla and has an electrode for defibrillation between the arm and the chest. In this way, compression member 12 may be placed over the sternum, with end elements 18 and 20 being placed over the lower rib cage to stimulate the respiratory muscles to contract between chest compressions as previously described. When needed, defibrillation may be provided by actuating the electrode on end element 18a. Optionally, a defibrillation unit 52a may be coupled to device 10'. Unit 52a includes an energy source for both diaphragmatic pacing and defibrillation. In this way, the energy source and other electrical components may be included within device 10' or in unit 52a.

Figure 6:
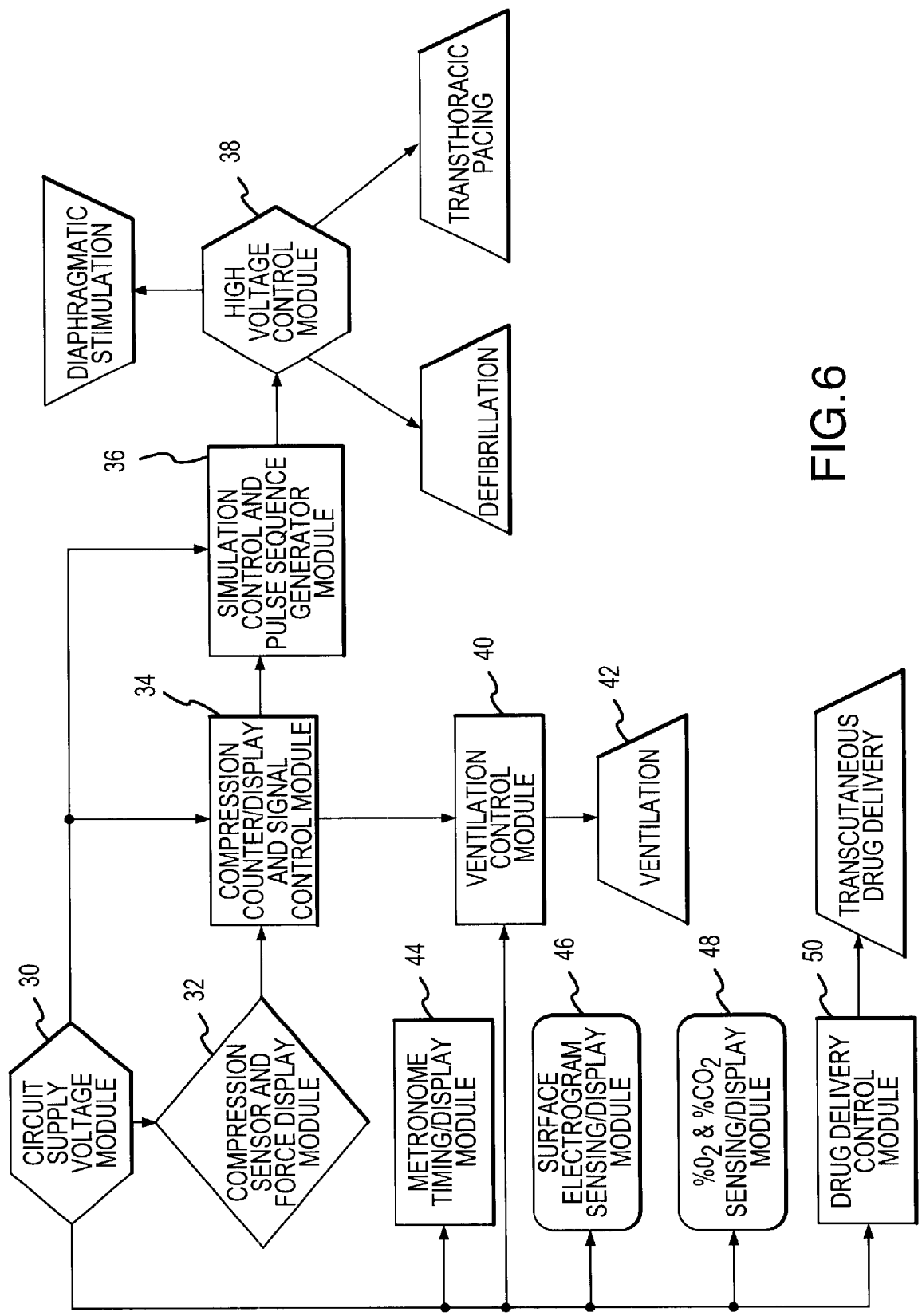
FIG. 6 is a block diagram of the circuitry of the device of FIG. 1 according to the invention.

Referring now to FIG. 6, a schematic diagram of the electrical components employed with device 10 will be described. Electrical power is provided to the various components with a circuit supply voltage module 30. Module 30 corresponds to energy source 28 of FIG. 4 and may comprise an internal or external power supply as previously described. A compression sensor and force display module 32 is provided to sense compression of compression member 12 (see FIG. 1) and to optionally display the force, pressure, and/or depth information to the rescuer. Exemplary compression sensors that may be employed include piezoelectric crystals that produce an electrical charge in proportion to the amount of force applied, fluid reservoirs and associated pressure sensors to detect an increase in pressure upon application of a force, strain gauges, and the like. Conveniently, the force detected by the compression sensor may be displayed on an LCD, LED or other display on device 10.

A compression counter/display and signal control module 34 is coupled to compression sensor 32 and counts each compression of compression member 12. The number of compressions may conveniently be displayed on device 10. Signals from module 34 are also transferred to a stimulation control and pulse sequence generator module 36 which is responsible for producing electrical signals employed by electrodes 22 (see FIG. 3). Module 36 is configured to produce an electrical pulse immediately after receipt of a counting logic signal from module 34. In this way, the electrodes may be actuated immediately after the compressive force is applied by the rescuer so that respiratory muscle stimulation is triggered to occur at the beginning of the relaxation or decompression phase of CPR. Module 36 preferably includes a signal generator to produce pulsed sequences resulting in the delivery of energy through the electrodes. Module 36 may be configured to produce pulses which correlate to every signal received from module 34 or only for selected signals from module 34. In this way, respiratory muscle stimulation may occur immediately after every compression or only after certain compressions.

In electrical communication with module 36 is a high voltage module 38 which functions to provide high voltage and/or high current waveforms so that the electrodes may operate at the proper stimulation voltage and/or current level. Module 38 may be employed to operate the electrodes to provide respiratory muscle stimulation as shown. The applied voltage and/or current may be modified by the rescuer by operating potentiometer 26 (see FIG. 4). Additionally, module 38 may be employed to operate the electrodes so that they perform a defibrillation function or to accomplish transthoracic cardiac pacing as is known in the art. In this way, device 10 may be used to stimulate the respiratory muscles to contract during CPR as well as for cardiac defibrillation or transthoracic cardiac pacing.

Also in electrical communication with module 34 is a ventilation control module 40. Module 40 is optional and may be provided to receive electrical signals from module 34 indicating actuation of compression sensor 32. Module 40 is coupled to a ventilation device 42 which may be configured to periodically ventilate the patient in an automated manner based on actuation of compression sensor 32 as CPR is being performed. Preferably, module 40 will be configured to actuate the ventilator at a frequency of about one ventilation to every five compressions. As one example, control module 40 may be constructed similar to the module described in U.S. Pat. No. 4,397,306 to coordinate the actuation of ventilation device 42 with actuation of compression sensor 32. The complete disclosure of this reference is herein incorporated by reference. Although device 10 has been described as being coupled to an automated ventilation device, it will be appreciated that manual ventilation devices and techniques may also be employed to ventilate the patient during the performance of CPR, whether or not electrically coupled to device 10. One advantage of providing ventilation control module 40 is that ventilation device 42 and high voltage/high current control module 38 are electrically coupled so that coordination of ventilation, diaphragmatic pacing, cardiac pacing, and/or defibrillation may occur.

Device 10 may be modified so that the electrical components (such as those set forth in FIG. 6) and power source are provided in a separate unit. For example, such components may be incorporated into a defibrillator which in turn is coupled to device. In this way, device 10 may be manufactured relatively inexpensively, with the electrical components being provided in a separate unit. Further both diaphragmatic stimulation and pacing may be provided with a base unit which is coupled to device 10.

In one particular alternative, patient ventilation may be assisted with the use of a ventilation device having a threshold negative intrathoracic pressure device which opens when a predetermined negative intrathoracic pressure is reached during the relaxation or decompression phase as described in U.S. Pat. Nos. 5,692,498 and 5,551,420, previously incorporated by reference. With such a configuration, device 10 may be provided with a controller which is coupled to the threshold valve so that actuation of the threshold valve may be coordinated with diaphragmatic stimulation to optimize the negative intrathoracic pressure. In particular, the impedance threshold valve may be opened and closed using a servo- or electromagnetically-controlled circuit that is coupled to device 10 so that its operation may be coordinated with operation of the electrodes.

Still referring to FIG. 6, a metronome timing display module 44 is electrically coupled to circuit supply high voltage/high current module 30 and is employed to produce regular audible and/or visual signals to assist the rescuer in performing regular chest compressions. A surface electrogram sensing/display module 46 is also electrically coupled to module 30 and allows for the sensing of surface electrograms and displaying the sensed information. Exemplary sensors for sensing surface electrograms include needles that are inserted through the skin, electrode-gel coupled sensors, and the like. A gas sensing display module 48 is provided to sense and display the amount of various gases in a patient's blood, airway, or skin/cutaneous surface. For example, module 48 may be employed to sense the amount of oxygen saturation, $CO_2$ saturation, and the like. Optionally, module 48 may include a thermistor or thermocouple-based temperature measuring device that may be placed against or inserted into the skin to measure the patient's body temperature.

A drug delivery control module 50 may optionally be provided to supply various drugs to the patient. For example, module 50 may be a passive device for delivering nitroglycerine. Alternatively, module 50 may be an active device for electrophoretic delivery of drugs such as vasopressin, an anti-arrhythmic drug, and the like. In this way, module 50 provides device 10 with the ability to transcutaneously deliver drugs as device 10 is placed against the patient's body to perform CPR.

Although one embodiment illustrates the use of a compression member to sense when the chest is being compressed, it will be appreciated that other techniques may be provided to sense chest compression. For example, electrodes may be placed on the chest and sensors employed to detect electrical impulses or a change in impedance as the chest is compressed. Alternatively, a pressure sensor may be provided in an airway device to detect an increase in airflow in the patient's airway. The electrodes may be coupled to an external defibrillator-pacer that is capable of delivering low energies, i.e. about 0.01 amps to about 2 amps, and more preferably about 0.1 amps to about 2.0 amps, to stimulate the diaphragm or other respiratory muscles. In this way, a system is provided which may provide respiratory muscle stimulation (that is coordinated with chest compressions), pacing, and defibrillation.

Figure 7:
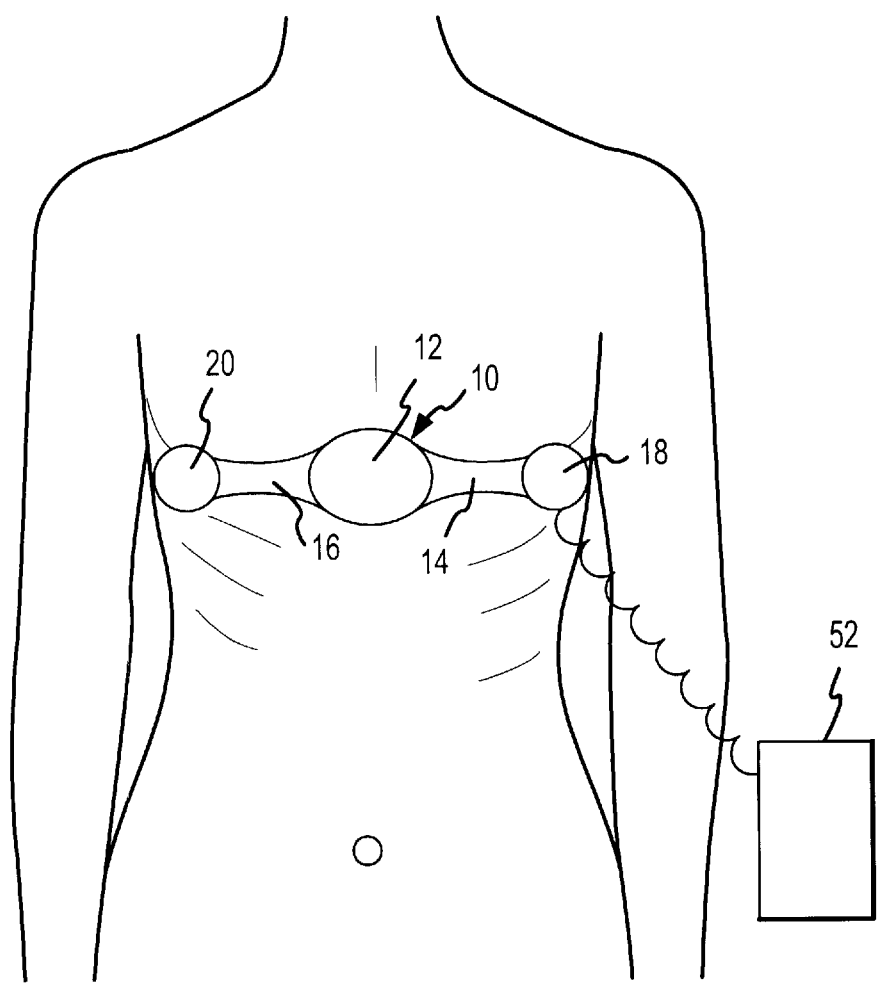
FIG. 7 illustrates the device of FIG. 1 when used to treat a patient according to the invention.

Referring now to FIG. 7, an exemplary method for performing CPR using device 10 will be described. As shown, device 10 is placed on the patient such that compression member 12 is placed over the sternum and end elements 18 and 20 are placed over the ribs. As previously described, the particular location and arrangement of end elements 18 and 20 may be varied to optimize respiratory muscle stimulation. The rescuer then compresses compression member 12, preferably by placing both hands on compression member 12 and pushing downward. Compression of compression member 12 proceeds in a manner similar to that performed when performing traditional CPR. Immediately after the maximum compression is applied, electrodes on end elements 18 and 20 are actuated to stimulate the diaphragm and/or the chest wall muscles to contract during the relaxation or decompression phase. Conveniently, power is supplied to the electrodes via an external defibrillator 52, although other energy sources may be employed as previously described. The electrodes may be actuated during every relaxation or decompression phase or during only selected relaxation or decompression phases, depending on the need of the patient. Since device 10 is coupled to the defibrillator 52, the patient may also be supplied with a defibrillation shock or cardiac pacing. Hence, defibrillator 52 may be used to stimulate respiratory muscle contraction as well as to pace and/or defibrillate the heart. In that case, the sensor may be configured to be the same electrodes used to defibrillate the patient so that no compression member would be needed.

To stimulate respiratory muscles to contract, the current supplied by the electrodes is preferably in the range from about 0.01 amps to about 2.5 amps, and more preferably from about 0.1 amps to about 1.0 amps. However, it will be appreciated that the specific amount of current will depend on chest wall impedance and mode of stimulation, e.g., square wave impulse, unipolar wave forms, biphasic wave forms, multiphasic wave forms, multi-vectorial pathways, use of pulse trains, and the like. In some cases it may be desirable to stimulate one side of the diaphragm or chest wall at a different time from the other side of the diaphragm or chest wall, e.g., by about 10 msec to about 200 msec, to reduce the risk of shock to the rescuer and to reduce inspiratory muscle fatigue. The respiratory muscles may be stimulated to contract at a frequency in the range from about 30 to about 120 times per minute. The timing sequence for stimulating different chest wall or other sites to induce inspiratory muscle contraction may be alternated to avoid muscle fatigue by varying the amplitude and duration of stimulation based upon a resistance or impedance measurement at any given stimulation site. Resistance measurements may be used in a closed loop circuit to help vary stimulation site location and stimulation outputs.

Periodically, about every one to ten compressions, the patient is ventilated. Ventilation may be accomplished using an automated ventilator which may or may not be coupled to device 10. Alternatively, various manual ventilators may be employed as is known in the art. In one particular embodiment, a ventilation device is coupled with a threshold valve so that the duration and extent of negative intrathoracic pressure may be controlled during the relaxation or decompression phase as previously described. A pressure sensor and feedback loop circuit may also be used to measure the negative intrathoracic pressure in the airway and adjust the energy delivered to the electrode to maintain a generally constant negative intrathoracic pressure caused by each contraction of the respiratory muscles.

Figure 8:
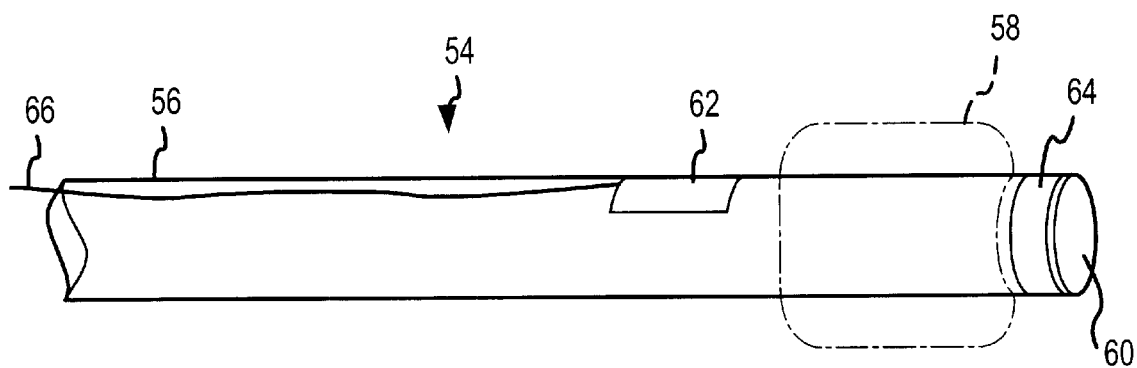
FIG. 8 illustrates an exemplary endotracheal tube having a pair of electrodes to electrically stimulate the phrenic nerve according to the invention.
Figure 8B:
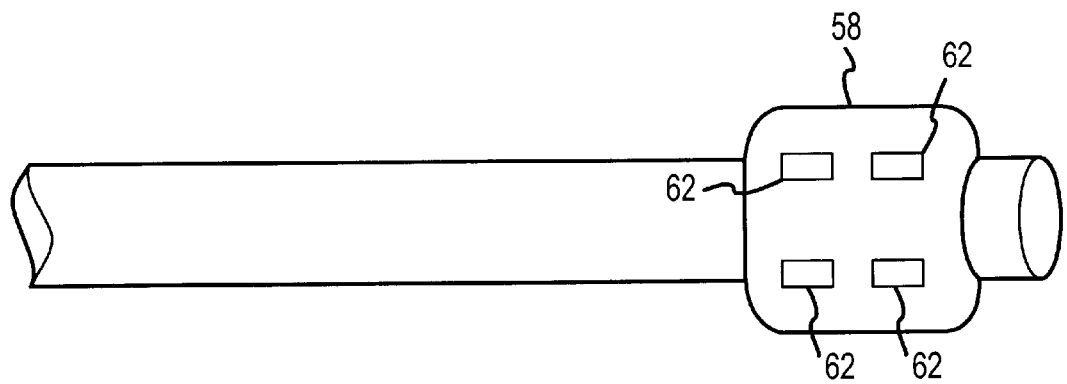
FIG. 8B illustrates the endotracheal tube of FIG. 8 having a plurality of electrodes disposed on an inflatable cuff according to the invention.

Referring now to FIG. 8, an alternative embodiment of a device 54 for stimulating the respiratory muscles to contract will be described. Device 54 comprises an endotracheal tube 56 having an inflatable member 58 (shown in phantom line) which serves to secure endotracheal tube 56 in the patient's airway as is known in the art. Endotracheal tube 56 includes a lumen 60 through which the patient is ventilated. Device 54 further includes a pair of electrodes 62 and 64 which operate in a bipolar manner to electrically stimulate the phrenic nerve, although other numbers and arrangements of electrodes may be employed, including monopolar electrode configurations. Electrode 62 or a plurality of electrodes may also be attached to inflatable cuff 58 as shown in FIG. 8B. In turn, stimulation of the phrenic nerve causes the diaphragm and chest wall muscles to contract. An electrical lead 66 is provided to supply electrical current to electrode 62.

In this way, when device 54 is inserted into the patient's airway, electrodes 62 and 64 are positioned so that when current is supplied to electrode 62, the phrenic nerve is electrically stimulated to cause the diaphragm muscles to contract. As with other embodiments described herein, electrode 62 is preferably actuated during the relaxation or decompression phase of CPR so that the respiratory muscles contract to increase the magnitude and extent of negative intrathoracic pressure during the decompression phase. Optionally, lead 66 may be coupled to a controller of a compression device which is similar to compression member 12 so that electrical stimulation of the phrenic nerve may be coordinated with chest compression. In a similar manner, lead 66 may be coupled to a ventilator which supplies air through lumen 60 so that ventilation may also be coordinated in a manner similar to that described with previous embodiments. Further, an impedance valve may be coupled to the endotracheal tube as described in U.S. Pat. Nos. 5,551,420 and 5,692,498, previously incorporated by reference.

In another alternative, endotracheal tube 54 may be provided with electrodes to also pace the heart. Such electrodes may be configured in a bipolar or monopolar manner, and may optionally be connected with an external electrode or an esophageal electrode.

Although described in the context of an endotracheal tube, it will be appreciated that electrical stimulation of the phrenic nerve may be accomplished by placing electrodes on a laryngeal mask airway, or other ventilation device which is placed within the larynx, esophagus, or trachea. Further, one or more electrodes may be included on a laryngeal mask airway or endotracheal tube that is inserted into the esophagus to pace the heart and/or to stimulate the phrenic nerve. As one example, such an electrode may be placed on an airway as described in U.S. Pat. No. 5,392,774, the disclosure of which is herein incorporated by reference. As another alternative, an electrical stimulator may be placed externally over the neck to stimulate the phrenic nerve. In still a further alternative, a magnetic field may be produced about the phrenic nerve to stimulate the diaphragm or chest wall muscles to contract. Devices for producing such an electrical field may be placed within the airway or externally about the neck.

Figure 8A:
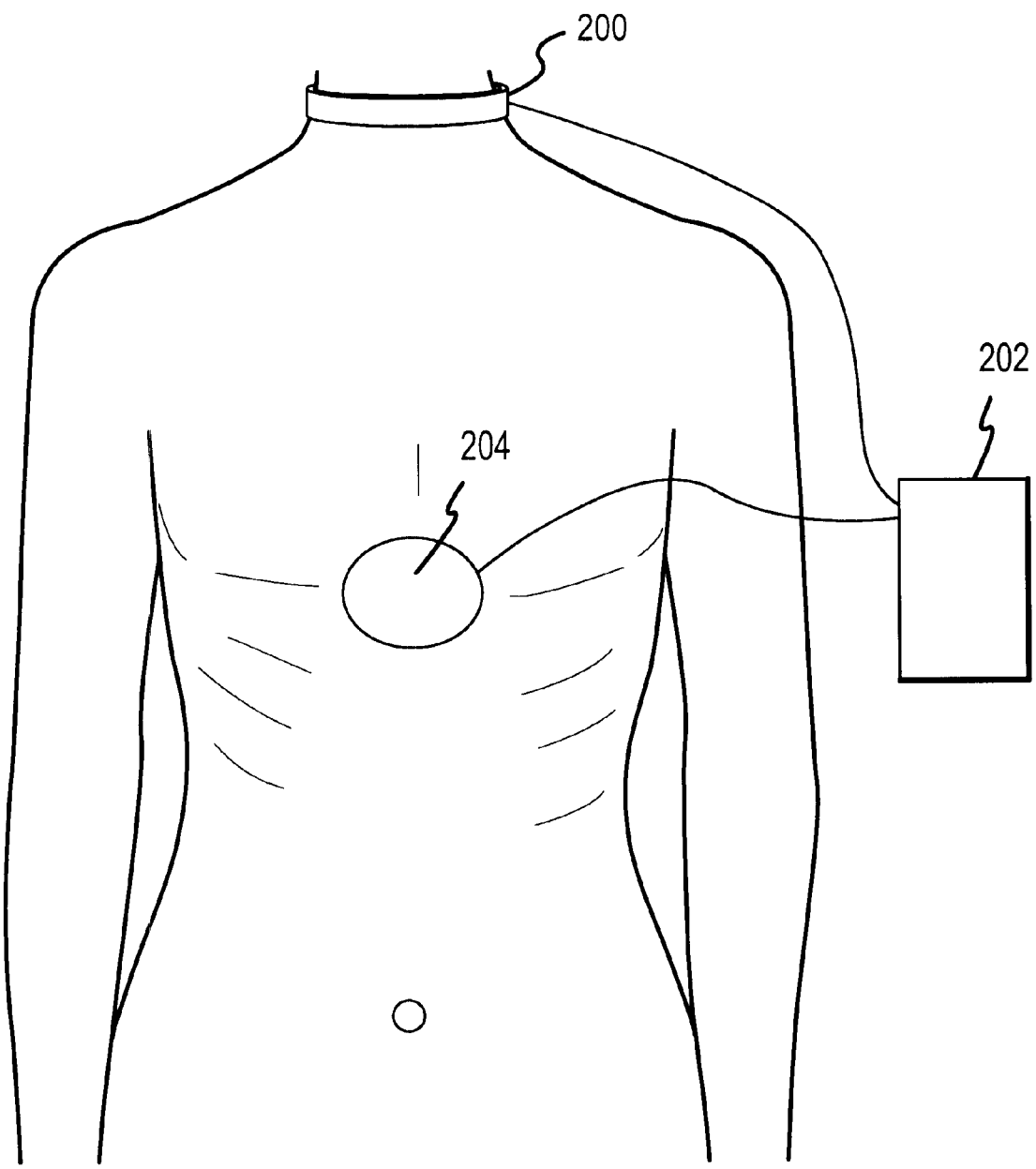
FIG. 8A illustrates a collar to electrically or magnetically stimulate diaphragmatic stimulation according to the invention.

One particular embodiment of a device 200 for either electrically or magnetically stimulating the phrenic nerve is illustrated in FIG. 8A. Device 200 comprises a collar having one or more electrodes or elements to produce electrical current or a magnetic field to stimulate the phrenic nerve. Device 200 is coupled to a controller 202 having a power source. Also coupled to controller 202 is a compression sensor 204 so that respiratory muscle stimulation may be coordinated with chest compressions as previously described.

In one alternative, the collar of device 200 may comprise a type of collar commonly used to rapidly stabilize the neck and/or help to tilt the head backwards. For example, such collars are often used in trauma situations to provide stability or to open a patient's airway. Such a collar may include at least two electrodes that are positioned such that they are anterior and posterior to the cervical vertebrae C3 to C6 when the collar is secured about the patient's neck. These electrodes may then be coupled to controller 202 to stimulate the phrenic nerve according to any of the techniques described herein.

In one particular embodiment, the invention may employ the use of a mechanical chest compressor which is coupled to a ventilator as described in U.S. Pat. No. 4,397,306, previously incorporated by reference. The stimulating electrodes may be coupled to the chest compressor or ventilator via a controller so that the controller may coordinate chest compression, ventilation, respiratory muscle stimulation, defibrillation, pacing, as well as other features previously described. Further, the amount of negative intrathoracic pressure generated with each contraction of the respiratory muscles may be used to adjust the energy needed for subsequent contractions. Such a system may conveniently be located in an emergency vehicle or a health care facility.

Figure 9:
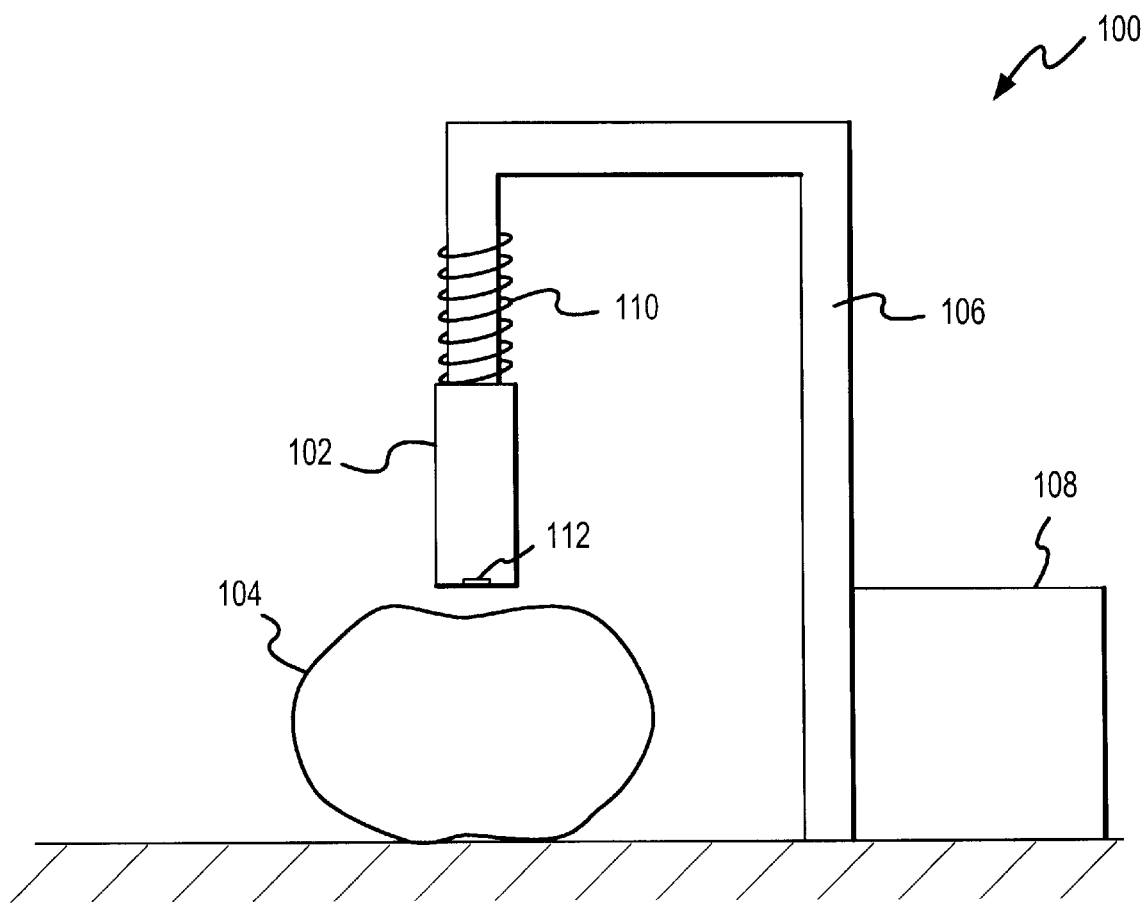
FIG. 9 is a schematic diagram of an exemplary system for stimulating the respiratory muscles to contract while performing CPR.

For example, one such system 100 is illustrated schematically in FIG. 9 and comprises a compression piston 102 that is held over a patient's thorax 104 by a support arm 106. Compression piston 102 is powered by an electric or pneumatic motor 108. When in use, piston 102 moves downward to compress the patient's chest. After the compression phase is complete, a spring 110, or other return mechanism, lifts piston 102 from the patient's chest to maximize the negative intrathoracic pressure during the relaxation phase. A controller is included with motor 108, and piston 102 includes a sensor 112 so that the respiratory muscles may be triggered to contract during the relaxation or decompression phase. The controller may optionally be coupled to a ventilator, a defibrillator, a heart pacer, a drug delivery system, various other sensors and/or an airway occluding device as previously described.

Figure 10:
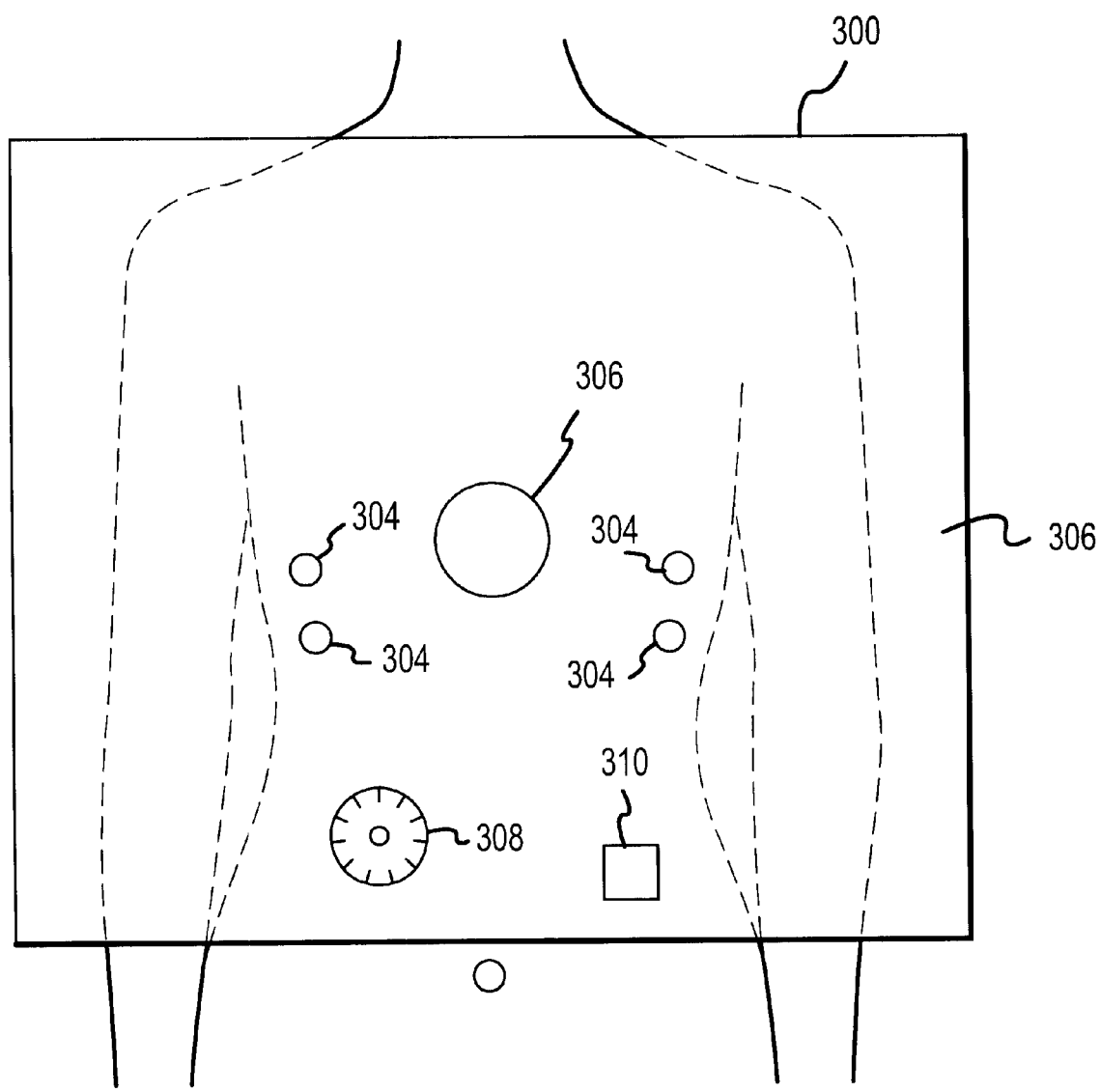
FIG. 10 illustrates a blanket having electrodes for stimulating the respiratory muscles to contract according to the invention.
Figure 11:
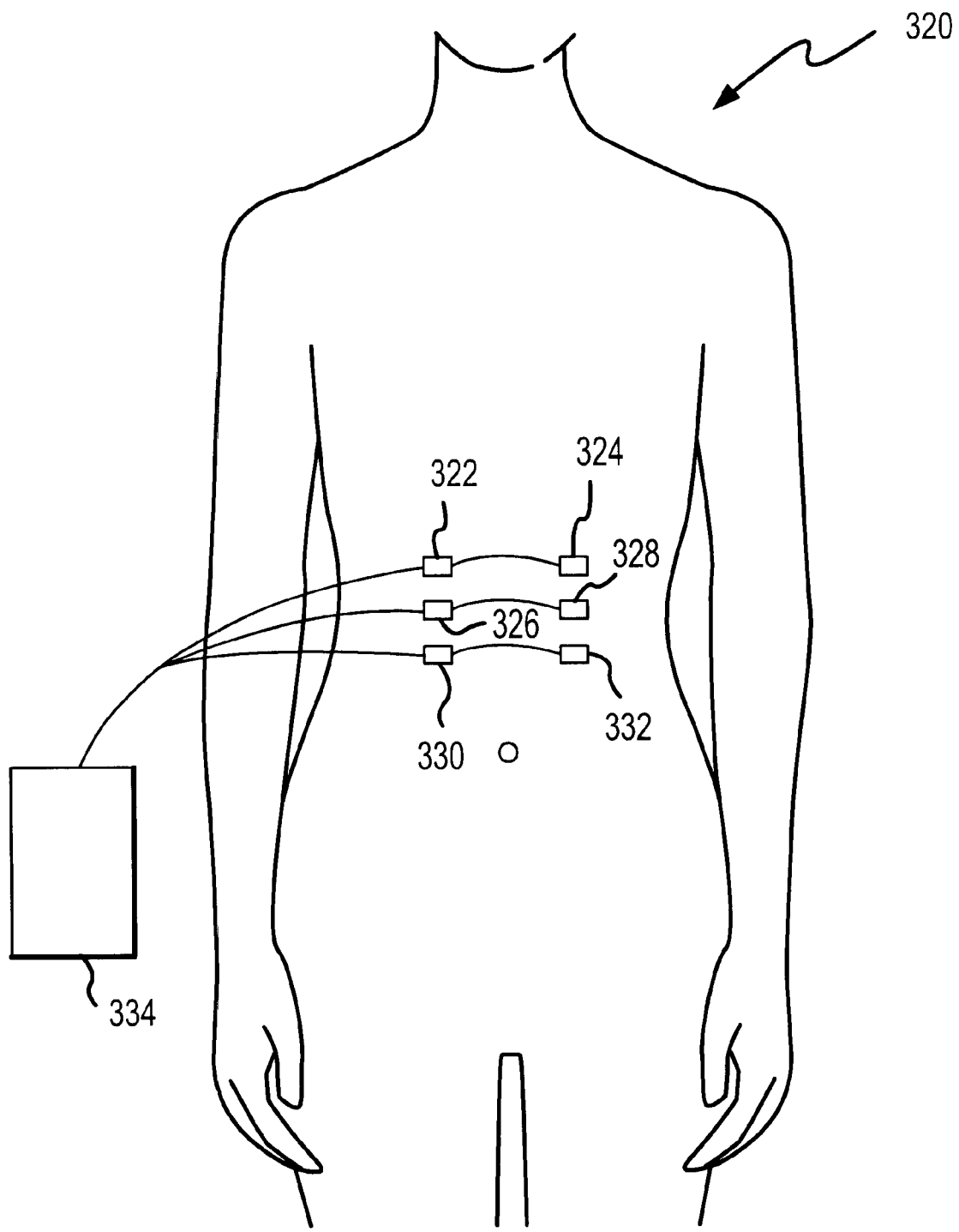
FIG. 11 schematically illustrates a system for stimulating the abdominal muscles according to the invention.

Still another embodiment of a device 300 for stimulating the respiratory muscles to contract is illustrated in FIG. 10. Device 300 comprises an insulated blanket 302 which is constructed of an electrically insulative material, such as rubber, to protect the rescuer against possible shocks. Blanket 302 may incorporate any of the elements of other embodiments described herein to assist in respiratory muscle stimulation, monitoring, drug delivery, sensing, defibrillation, pacing, and the like. For example, blanket 302 includes electrodes 304 which may be selectively located to stimulate respiratory muscle stimulation. For example, electrodes 304 may be placed over the lower margin of the rib cage as previously described, or over the abdomen to stimulate the abdomen. A compression sensor 306 is provided to coordinate chest compressions with activation of electrodes 304. A potentiometer 308 is included to regulate the amount of current supplied by electrodes 304. A power supply 310 is further provided to supply current to electrodes 304.

Referring now to FIG. 1, a stimulation system 320 will be described. System 320 includes multiple leads 322–332 that are arranged in pairs. Although shown with six leads, it will be appreciated that other numbers and arrangements may be employed. For example, leads may be placed onto the patient's back. Leads 322–332 are arranged so that pairs of the leads may be sequentially actuated to produce a wave of contractions forcing venous blood back into the thorax and causing the diaphragm to be pushed upward to lead to respiratory gas exhalation. For example, leads 330 and 332 may first be actuated, followed by actuation of leads 326 and 328, and followed by actuation of leads 322 and 324.

The leads are coupled to a controller/power source 334 to supply current to the leads and to control when the leads are actuated. Conveniently, controller 334 may be configured similar to the controllers and/or other electrical circuitry that are associated with the various inspiratory muscle stimulator systems described herein. In some cases, controller 334 may be incorporated into or coupled with these inspiratory stimulation controllers and/or electrical circuitry to coordinate alternating inspiratory muscle and abdominal musculatory contraction. Further, such a controller may be configured to control the timing sequence of the leads so that the abdominal stimulation occurs about half way into the inspiratory muscle stimulation phase. This typically occurs about half way into the chest wall decompression phase when chest compressions are performed.

Figure 12:
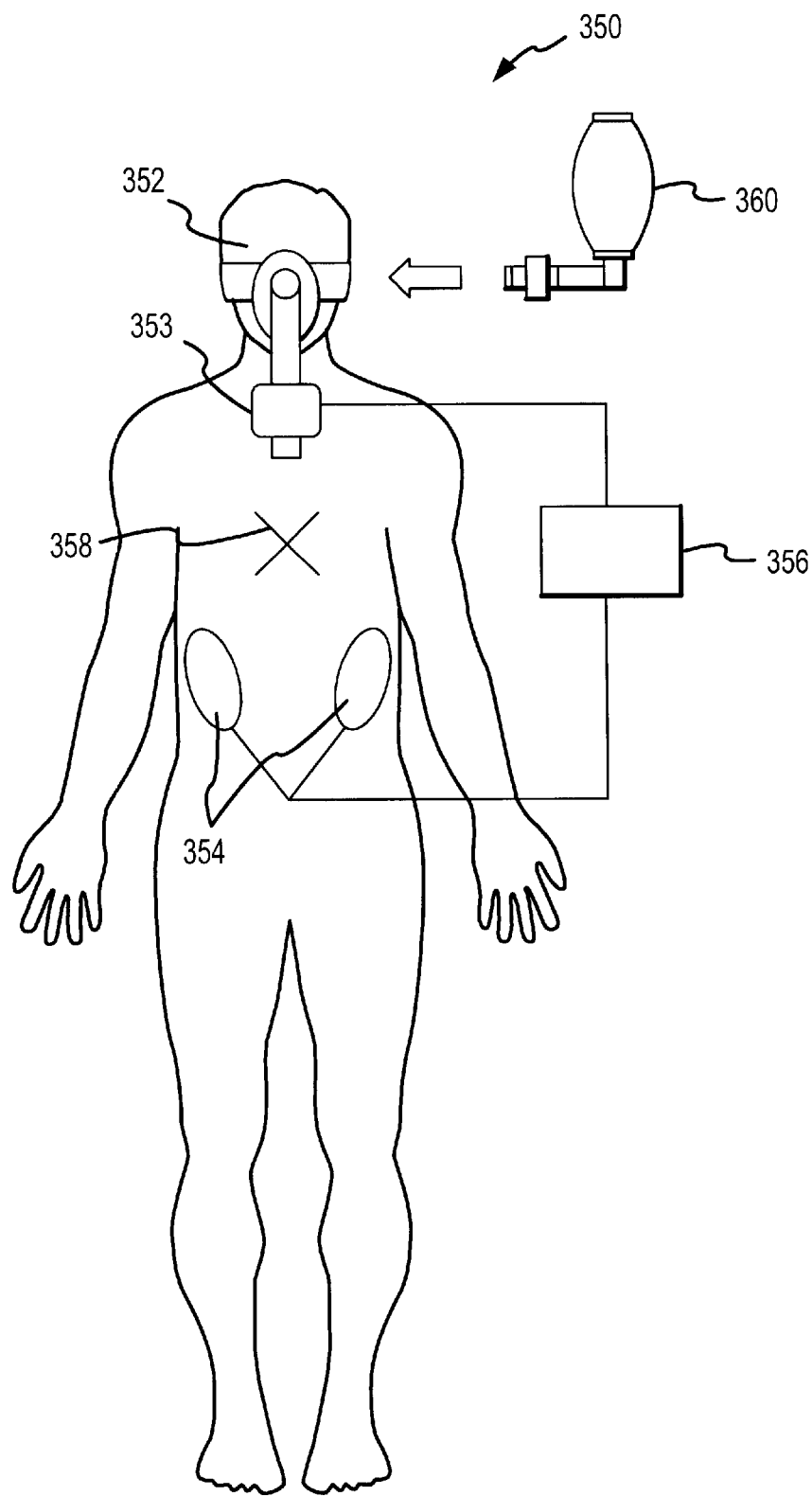
FIG. 12 illustrates a system for respiratory gas occlusion and abdominal stimulation according to the invention.
Figure 12A:
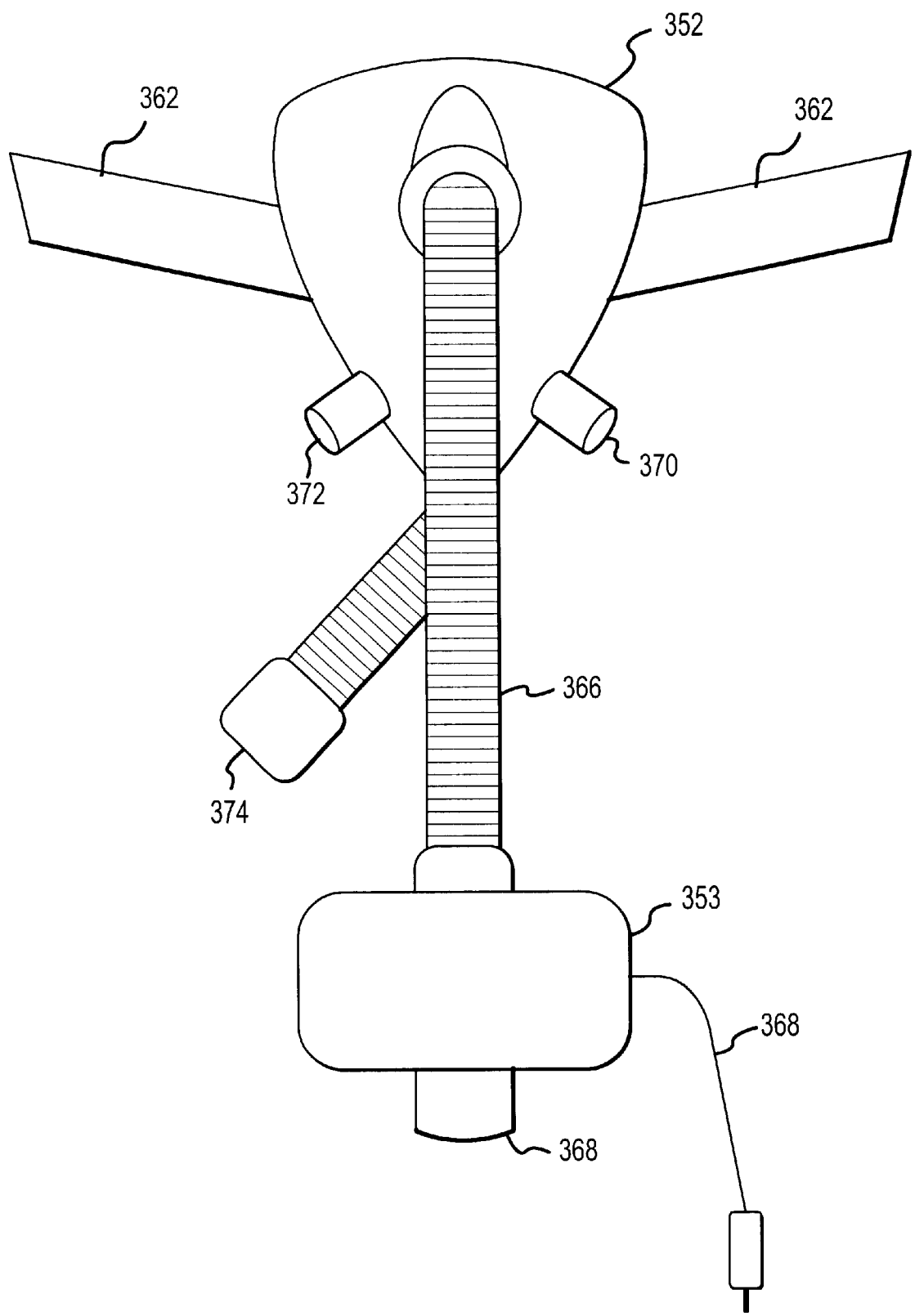
FIG. 12A illustrates a facial mask of the system of FIG. 12.
Figure 12B:
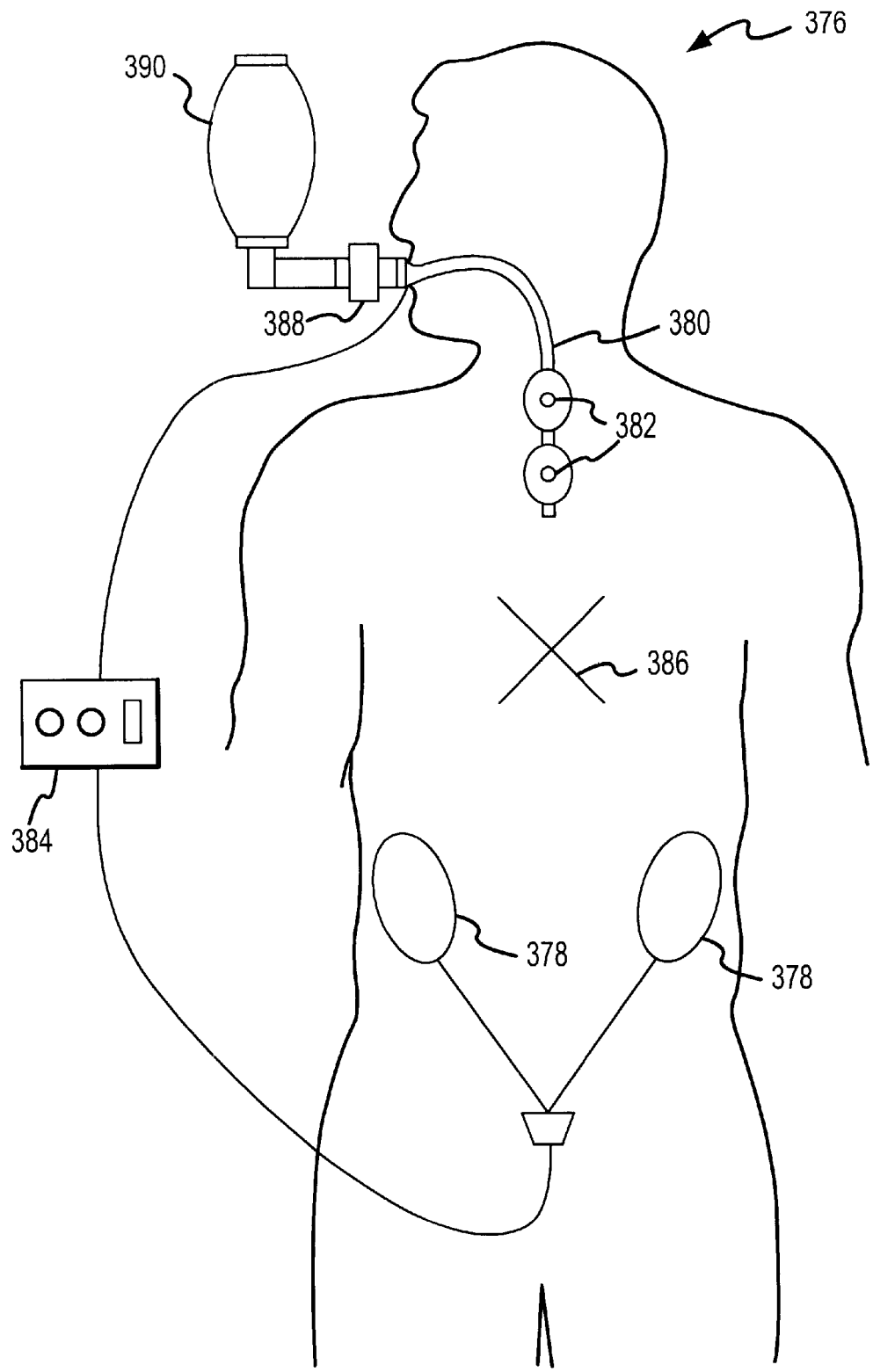
FIG. 12B illustrates an endotracheal/abdominal stimulation system according to the invention.

FIGS. 12, 12A and 12B illustrate devices or systems used to simultaneously cause an increase in intra-abdominal pressure and transient airway occlusion to induce an electrical cough, thereby promoting blood out of the chest to the brain and out of the abdomen to the chest. When performed in connection with chest compressions, cardiac output is maintained by rhythmically increasing intrathoracic pressure against a closed airway with a simultaneous increase in abdominal pressure. Upon release of the abdominal stimulation and expiratory airway occlusion, followed by passive or active downward movement of the diaphragm, the chest is filled with air and both ventilation and cardiopulmonary circulation is induced.

Shown in FIG. 12 is a system 350 to produce a cough by periodic occlusion of respiratory gases and by abdominal stimulation. System 350 includes a respiratory face mask 352 having a pressure release valve 353 to transiently prevent respiratory gases from exiting the lungs to raise intrathoracic pressure. System 350 further includes one or more stimulation electrodes 354 that may be employed to stimulate inspiratory effort similar to that described with previous embodiments. Although shown on the abdomen, it will be appreciated that electrodes may be placed at other locations, such as on the neck or chest, to also stimulate the diaphragm to contract. Positioned between electrodes 354 and release valve 353 is a controller 356. In this way, opening of release valve 353 may be coordinated with actuation of electrodes 354. Also shown in FIG. 12 is a chest compression site 358 to indicate where chest compressions may optionally be performed. System 350 may optionally include a respiratory air bag 360 to periodically ventilate the patient.

In use, valve 353 is closed to prevent respiratory gases from exiting the patient. Electrodes 354 are actuated to increase intra-abdominal pressure. During stimulation of the abdominal muscles, valve 353 is abruptly opened to induce the patient to cough. In one aspect, valve 353 may be opened for a time in the range from about 10 ms to about 500 ms after the abdominal muscles are stimulated to contract. After coughing, air bag 360 may be used to ventilate the patient. Chest compressions and/or respiratory muscle stimulation may optionally be performed prior to each induced cough.

Referring now to FIG. 12A, mask 352 will be described in greater detail. Coupled to mask 352 are a pair of straps 362 that may be secured together about the patient's head to seal mask 352 to the patient's face. Conveniently, a material, such as Velcro, may be employed to hold the straps together. Extending from mask 352 is an expiration tube 366 which is coupled to valve 353. Also coupled to valve 353 is a connector 368 to allow valve 353 to be coupled to controller 356. Valve 353 may include an actuator that runs on DC voltage so that when an electrical signal is sent from controller 356, valve 353 is opened. Valve 353 further includes an expiratory gas port 368 to allow respiratory gases from the patient to be exhaled once valve 353 is opened.

Mask 352 also includes a pressure transducer port 370 which may include a pressure transducer to monitor the pressure within the patient. The transducer may be coupled to controller 356 (see FIG. 12) so that the pressure may be monitored. Mask 352 may further includes a safety pressure release check valve 372 that may be configured to open if the intrathoracic pressure becomes too great. Coupled to tube 366 is a ventilation bag valve connector 374 that allows air bag 360 (see FIG. 12) to be coupled to mask 352.

FIG. 12B illustrates an endotracheal/abdominal stimulation system 376. System 376 includes one or more electrodes 378 positioned on the abdomen to stimulate the abdominal muscles. An endotracheal tube 380 is also provided with one or more electrodes 382 to stimulate the diaphragm to contract. A controller 384 is provided to control actuation of both electrodes 378 and 382. In this way, diaphragmatic stimulation may be alternated with abdominal stimulation. Alternatively, a chest compression site 386 may be provided. However, external chest compressions may not be needed once an alternating inspiratory/abdominal muscle stimulation pattern is established. System 376 may optionally include a valve system 388. Valve system 388 may include a pressure release valve similar to valve 353 of FIG. 12A to induce the patient to cough. Valve system 388 may optionally include a threshold impedance valve and/or a threshold expiration valve similar to the valves described in U.S. Pat. Nos. 5,551,420 and 5,692,498 to augment negative and/or positive negative intrathoracic pressures. In this way, large increases and/or decreases in intrathoracic pressures may be obtained. System 376 may also optionally include a respiratory bag 390 to periodically supply respiratory gases to the patient.

Hence, in one aspect, the invention may utilize either the face mask system of FIG. 12 or the endotracheal tube system of FIG. 12B to periodically block the release of respiratory gases or to periodically block both expiratory and inspiratory gases. This may be done in combination with abdominal and/or diaphragmatic muscle stimulation. Chest compressions may also be performed, but may not be needed if an alternating inspiratory/abdominal muscle stimulation pattern is established.

Figure 13:
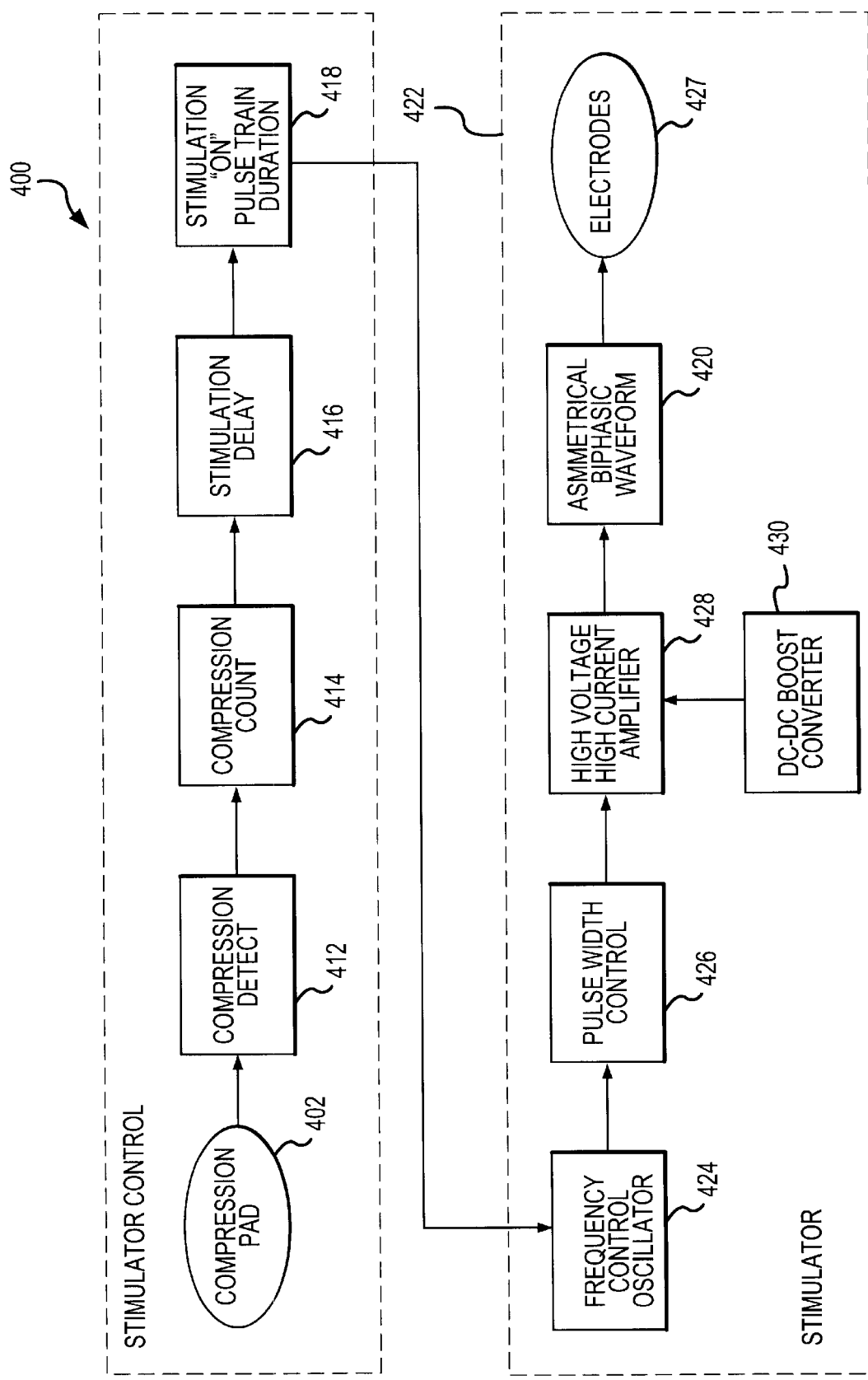
FIG. 13 is a circuit block diagram of a system for electrically stimulating the diaphragm according to the invention.

Referring now to FIG. 13, one embodiment of a system 400 that is particularly useful for unilateral or bilateral stimulation of the phrenic nerve will be described. System 400 is configured to sequentially initiate an action potential to cause diaphragmatic contractions. More specifically, system 400 is configured to initiate a "gasp" produced by contracting the diaphragm once a short duration stimulation pulse train is applied using surface electrodes. Optionally, system 400 may also be configured to electroventilate a patient by producing long duration stimulation pulse trains with a ramped increase in voltage or current output using the electrodes, thereby producing controllable respiratory tidal volumes greater than 500 ml.

System 400 may conveniently be described in terms of sensing, control, and output stages. The sensing stage comprises circuit components designed to sense when a chest compression is delivered to the patient. In cases where system 400 is used for electroventilation or for patients in shock, the sensing stage is designed to sense inspiratory effort. A variety of sensors may be employed to sense chest compressions and inspiratory effort, including force/pressure transducers, electromechanical switches, magnetic reed switches, and the like. As shown in FIG. 13, system 400 utilizes a compression pad 402 that houses the sensor. Compression pad 402 may be placed over the patient's sternum upon administration of CPR. Inspiratory effort sensors may be located on the patient's chest or in the inspiratory impedance valve.

Figures 14, 15:
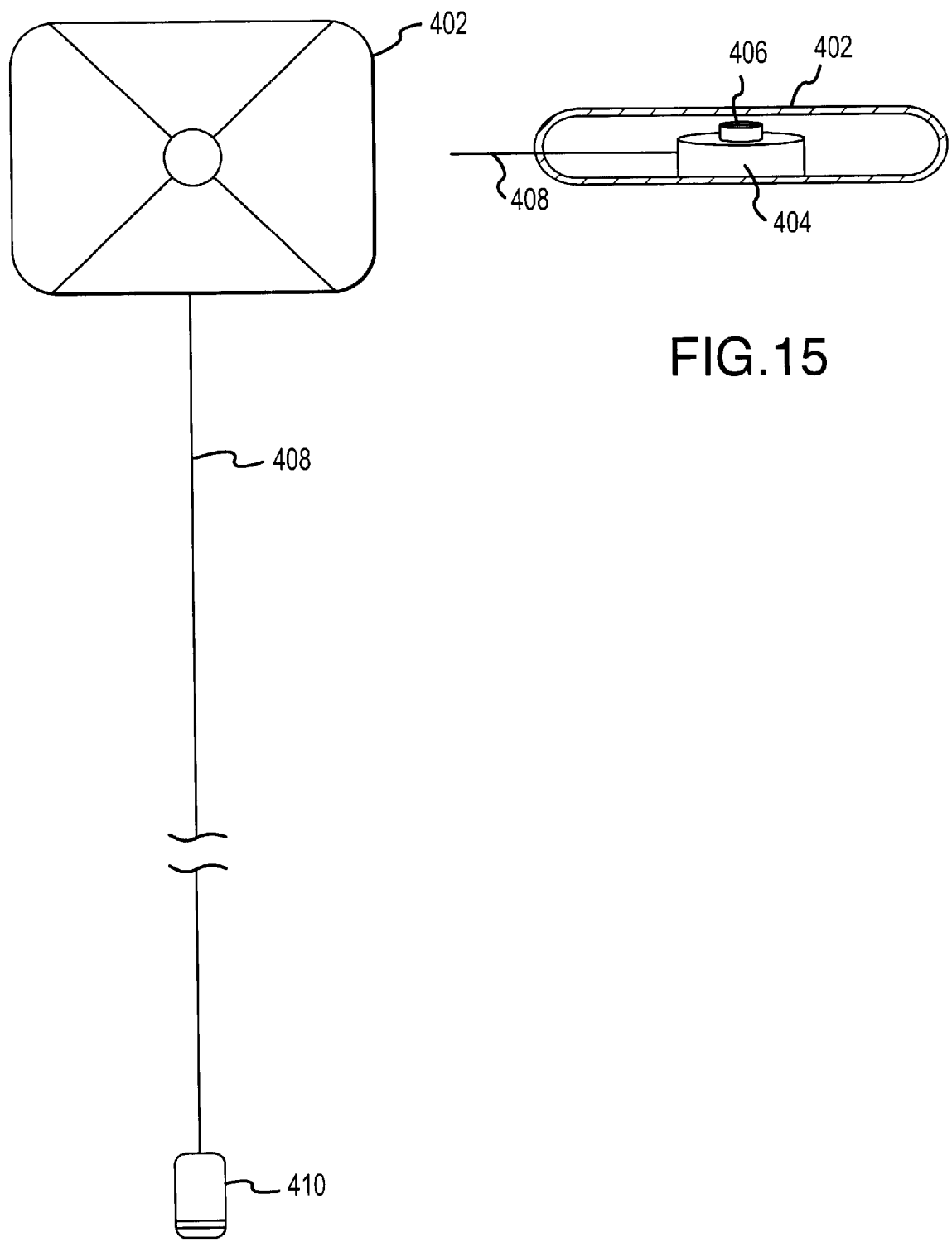
FIG. 14 is a top view of a compression pad that may be used with the system of FIG. 13.
FIG. 15 is a cross sectional side view of the compression pad of FIG. 14.

One embodiment of compression pad 402 is illustrated in FIGS. 14 and 15. As shown, a sensor 404 is disposed within pad 402 and includes a switch 406 that is depressed upon compression of pad 402 during the performance of CPR. A transmission cable 408 is coupled to sensor 404 to permit the transmission of a signal once a compression has been sensed. As best shown in FIG. 14, cable 408 is coupled to a cable connector 410 that permits sensor 404 to be electrically coupled with the sensing stage circuit components of system 400. Hence, once a chest compression is sensed, the signal is transferred via cable 408 to compression detect circuitry 412 of system 400 to indicate that a compression has been sensed. The signal is then transferred to the control stage of system 400 which includes: 1) compression count circuitry 414 to count the number of chest compressions, 2) stimulation delay circuitry 416 to delay initiation of the stimulation pulse, and 3) stimulation "ON" pulse duration circuitry 418 to initiate pulse duration or stimulator "ON" time. Delay circuitry 416 is configured to deliver the stimulation pulse train at the appropriate timing during the compression phase of CPR. However, it will be appreciated that the stimulation pulse train may be delayed to stimulate the patient at any time during the compression or decompression phases of CPR. Moreover, in some cases, system 400 may be configured to produce a repeating signal to indicate to the rescuer when to perform chest compressions. In such a case, stimulation delay circuitry 416 would not be needed.

Pulse train duration circuitry 418 is synchronously actuated with the delay circuitry to control the duration or pulse width of the pulse train. In other words, the pulse train duration controls the amount of time the stimulator is "ON" to deliver the pulse train to the electrodes. The pulse width of the pulse train may be adjusted to stimulate the patient during the decompression phase of CPR. However, it will be appreciated that the pulse width may be preset and/or adjusted to stimulate the patient during any segment of the compression or decompression phases of CPR. Further, as previously described, system 400 may be used in non-CPR applications, and pulse train duration circuitry 418 may be configured to produce an appropriate pulse train for the particular application.

Also actuated synchronously with stimulation delay circuitry 416 and pulse train duration circuitry 418 is compression count circuitry 414. Compression count circuitry 414 is configured to count the number of chest compressions and initiate the stimulation pulse train or "ON" time during the appropriate compression/decompression cycle. Merely by way of example, the counting circuitry may be preset to stimulate at 1:1, 2:1, or 3:1 compressions per stimulation pulse. If 2:1 is selected, the stimulation "ON" pulse train stimulates the patient once upon every other chest compression. If 3:1 is selected, the stimulation "ON" pulse train stimulates the patient once upon every third chest compression. Controlled pulse trains, once actuated to oscillate, are transferred to the output stage of system 400 that produces an asymmetrical biphasic wave form as shown in block 420.

To produce the biphasic wave form, system 400 includes a stimulator 422 that includes a frequency control oscillator 424 that receives the signal from pulse train duration circuitry 418. Frequency control oscillator 424 is employed to control the frequency of the electrical signal that is transferred to electrodes 427 of stimulator 422. A pulse width control circuit 426 is also provided to control the pulse width of the electrical signal. A high voltage, high current amplifier 428 and a DC-DC boost converter 430 are employed to convert the signal to a high voltage, high current DC signal which is then sent to electrodes 427. Merely by way of example, stimulator 422 may be employed to produce an asymmetrical biphasic wave form having a pulse width of about 300 microseconds, with controllable current amplification being in the range of about 100 milliamps to about 2,000 milliamps.

For patients in shock, system 400 may be configured so that the pulse is activated after each breath of the patient for about 0.25 to about 5 seconds. The ratio of breath to phrenic nerve stimulation may vary from 2:1 to about 1:5. Further, a threshold valve may be used to control the supply of respiratory gases to the lungs during treatment of both shock and CPR as previously described.

Figure 16:
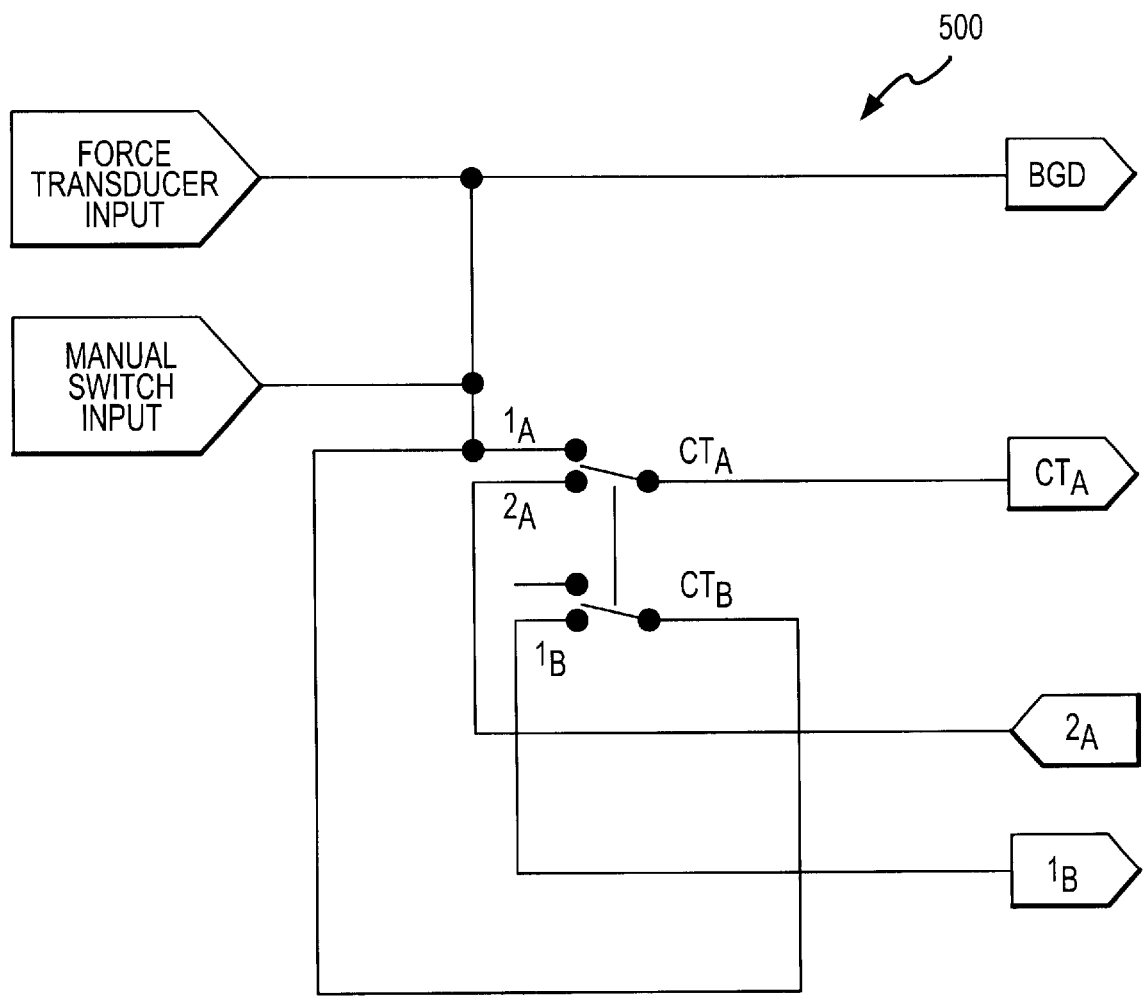
FIG. 16 illustrates a circuit diagram of an input control switch of the system of FIG. 13.

FIGS. 16–21 illustrate various circuit diagrams that may be used in constructing the stimulator control portion of system 400, it being appreciated that a variety of other circuits may be used to construct system 400. For example, FIG. 16 illustrates a circuit diagram of an input control switch 500 that is used to select the type of compression pad transducer, i.e. sensor 404 of FIGS. 14 and 15. This selection may be for a force/pressure transducer or a microswitch.

Figure 17:
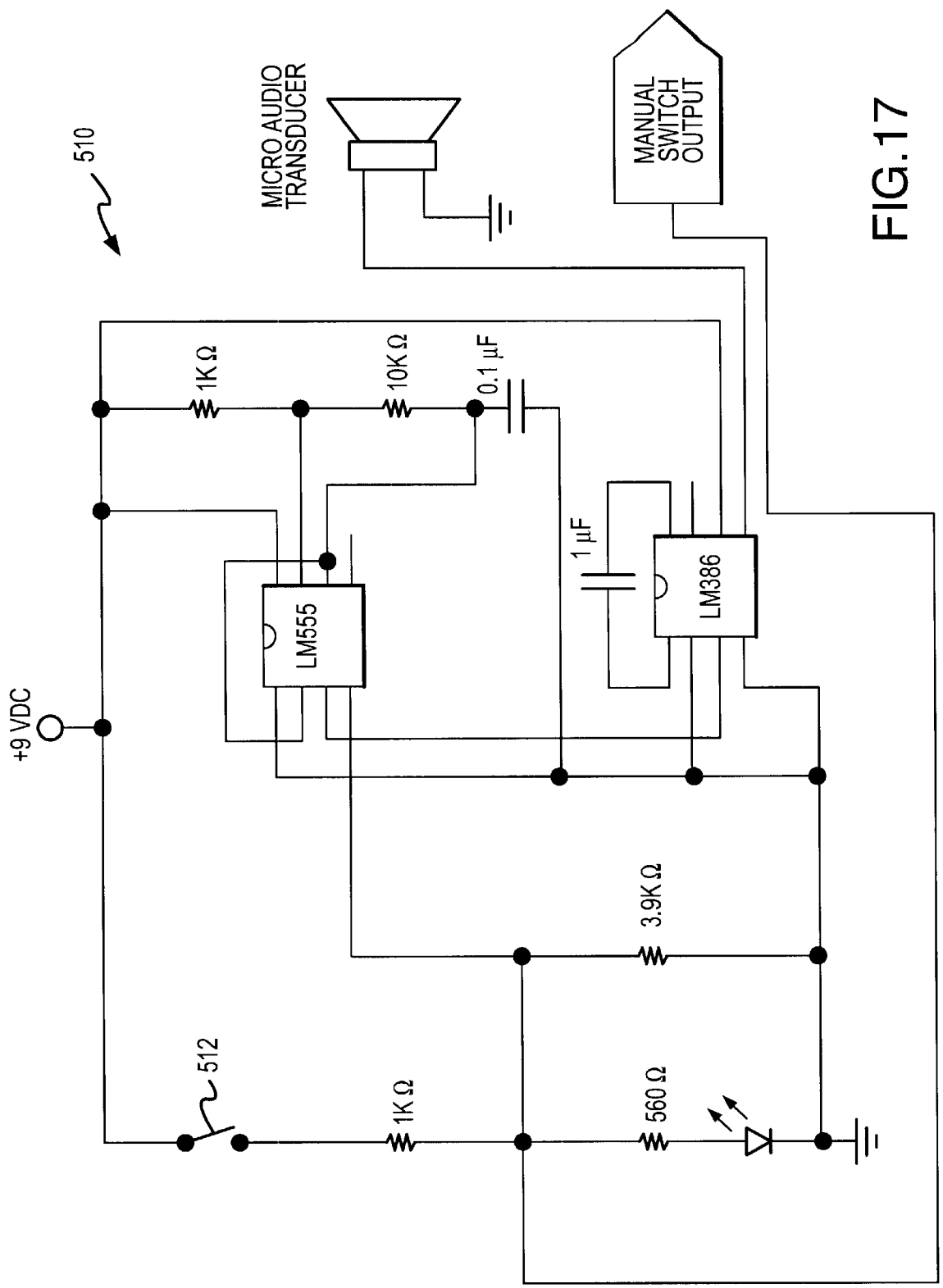
FIG. 17 illustrates a circuit diagram of a manual switch controller of the system of FIG. 13.

FIG. 17 illustrates a circuit diagram of a manual switch controller 510 that may be used in compression detect circuitry 412 of FIG. 13. Controller 510 functions to produce a visual light and an audible tone when a chest compression is detected via the compression pad. As such, controller 510 includes a switch 512 that would be housed in the compression pad of FIG. 15.

Figure 18:
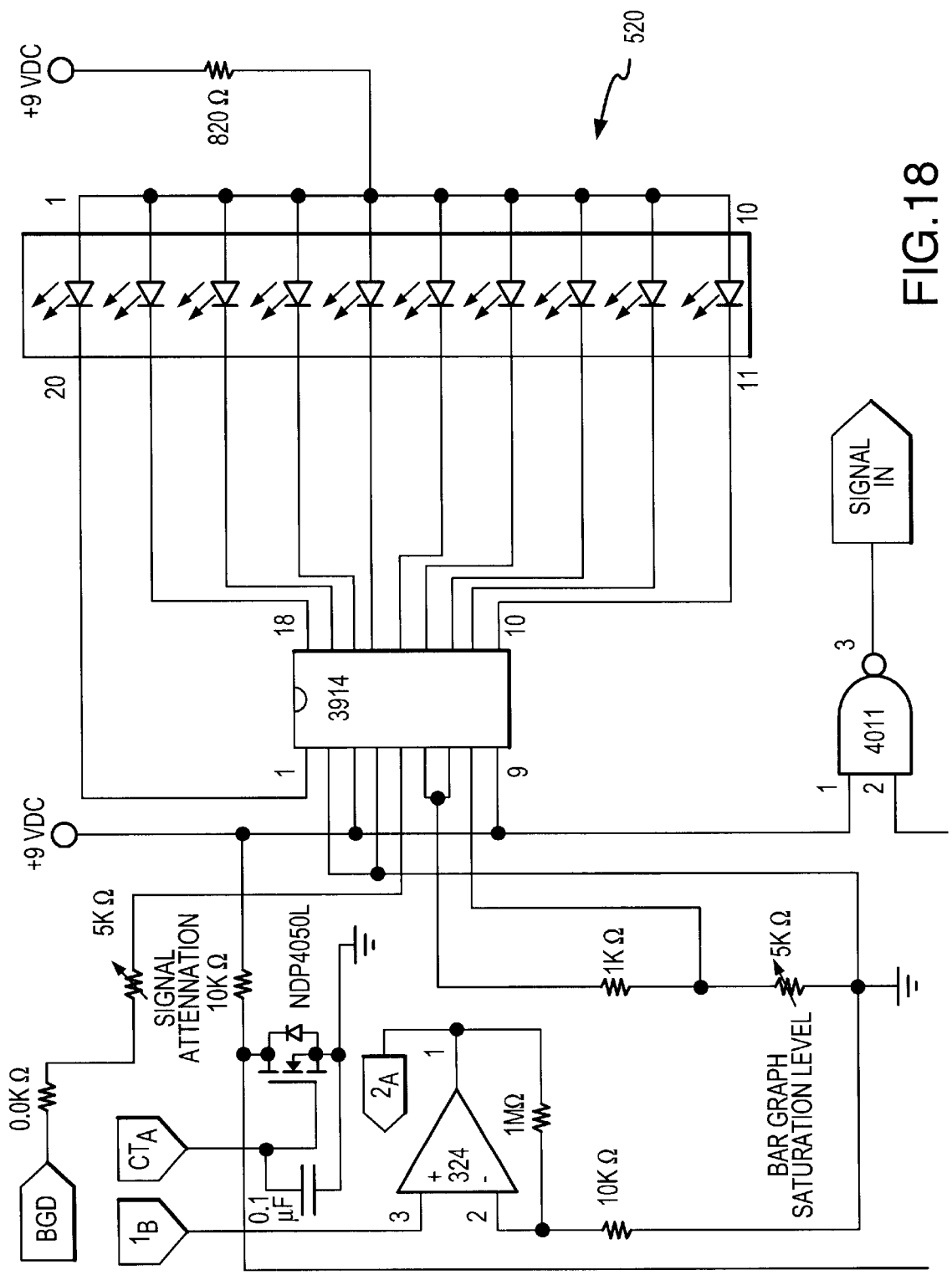
FIG. 18 illustrates a circuit diagram of an input signal and display module of the system of FIG. 13.

FIG. 18 illustrates a circuit diagram of an input signal and display module 520 that may also be used in constructing compression detect circuitry 412 of FIG. 13. Module 520 functions to display the strength of the chest compression if a force transducer is used within the compression pad, or displays that a chest compression occurred if a micro switch is used within the compression pad.

Figure 19:
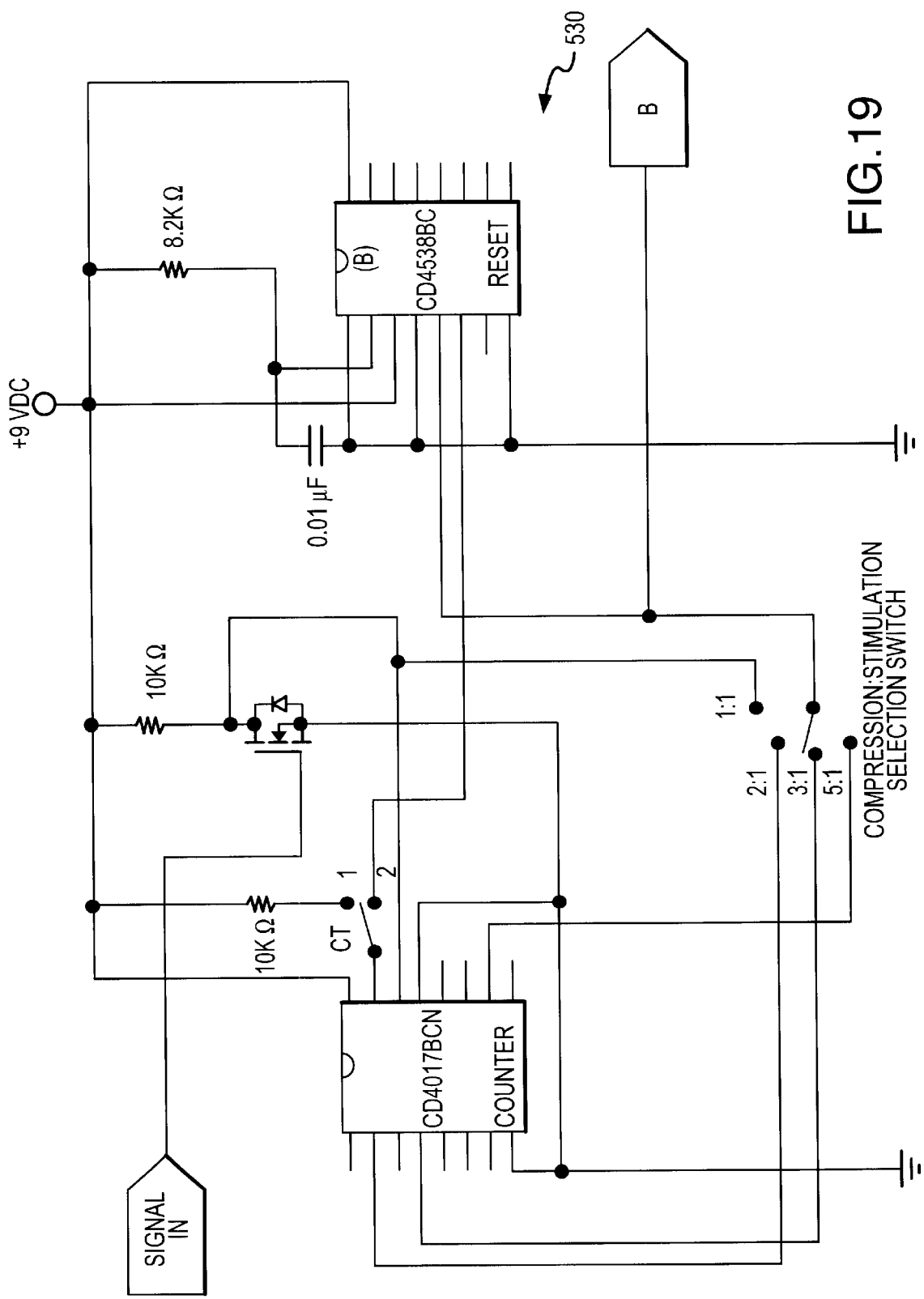
FIG. 19 illustrates a circuit diagram of a compression counter/reset module of the system of FIG. 13.

FIG. 19 illustrates a circuit diagram of a compression counter/reset module 530 that may be used in constructing compression count circuitry 414 of system 400. Module 530 is configured to count and reset the counter based upon the preselected compression: stimulation ratio. For example, if 2:1 is selected, the circuit detects two compressions, sends a stimulation "OK" signal to the delay circuit of FIG. 20 and resets the counter to begin the compression counting sequence over again.

Figure 20:
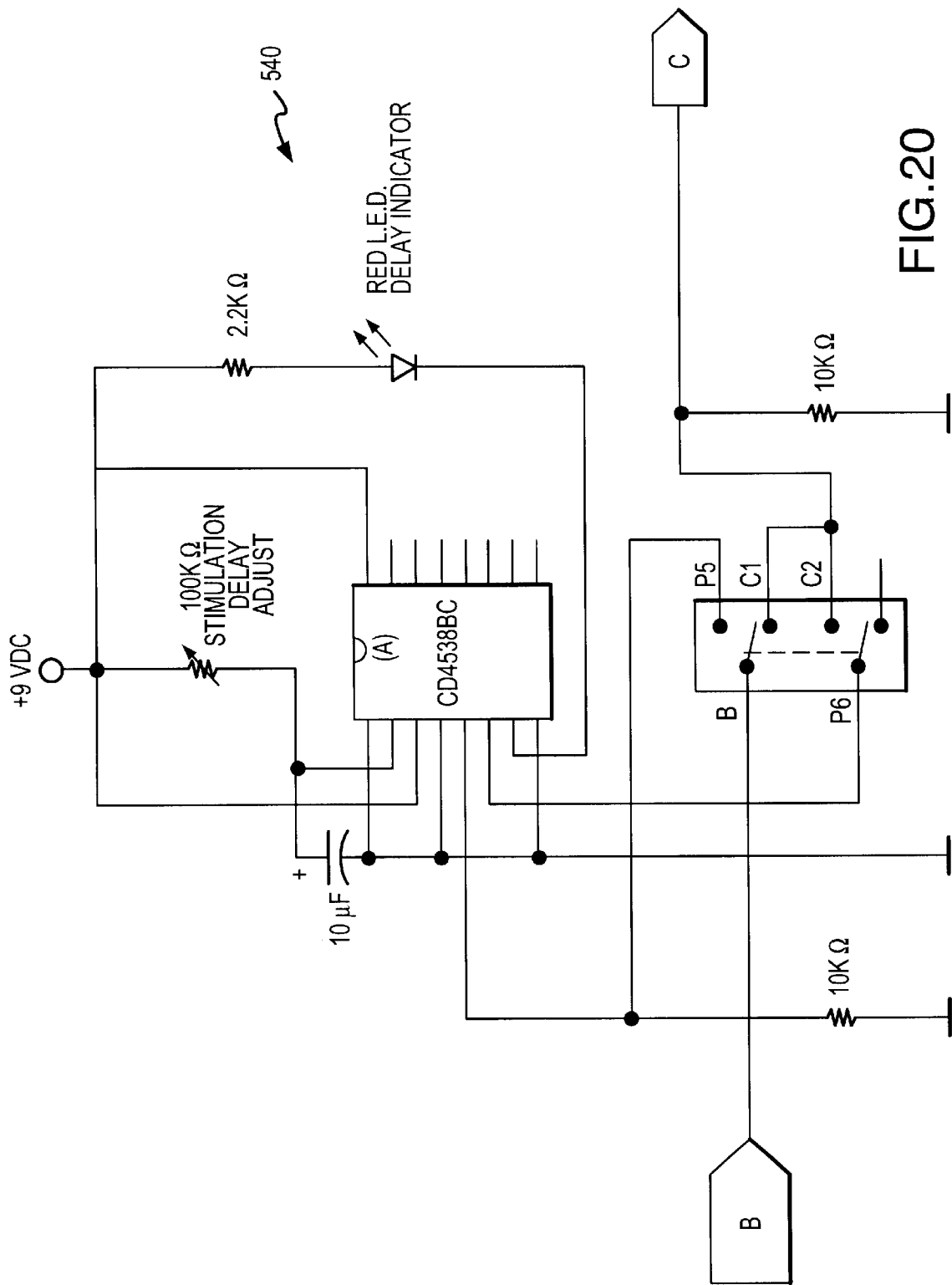
FIG. 20 illustrates a circuit diagram of a sense and display module of the system of FIG. 13.

As just mentioned, FIG. 20 illustrates a sense and delay module 540 that may be used to construct stimulation delay circuitry 416 of FIG. 13. Module 540 functions to delay when the stimulator is turned "ON" in reference to the decompression phase of CPR. Module 540 is a timing circuit triggered by the compression count circuitry of module 530 and may be adjusted to delay the stimulator "ON" pulse to any portion of the CPR cycle.

Figure 21:
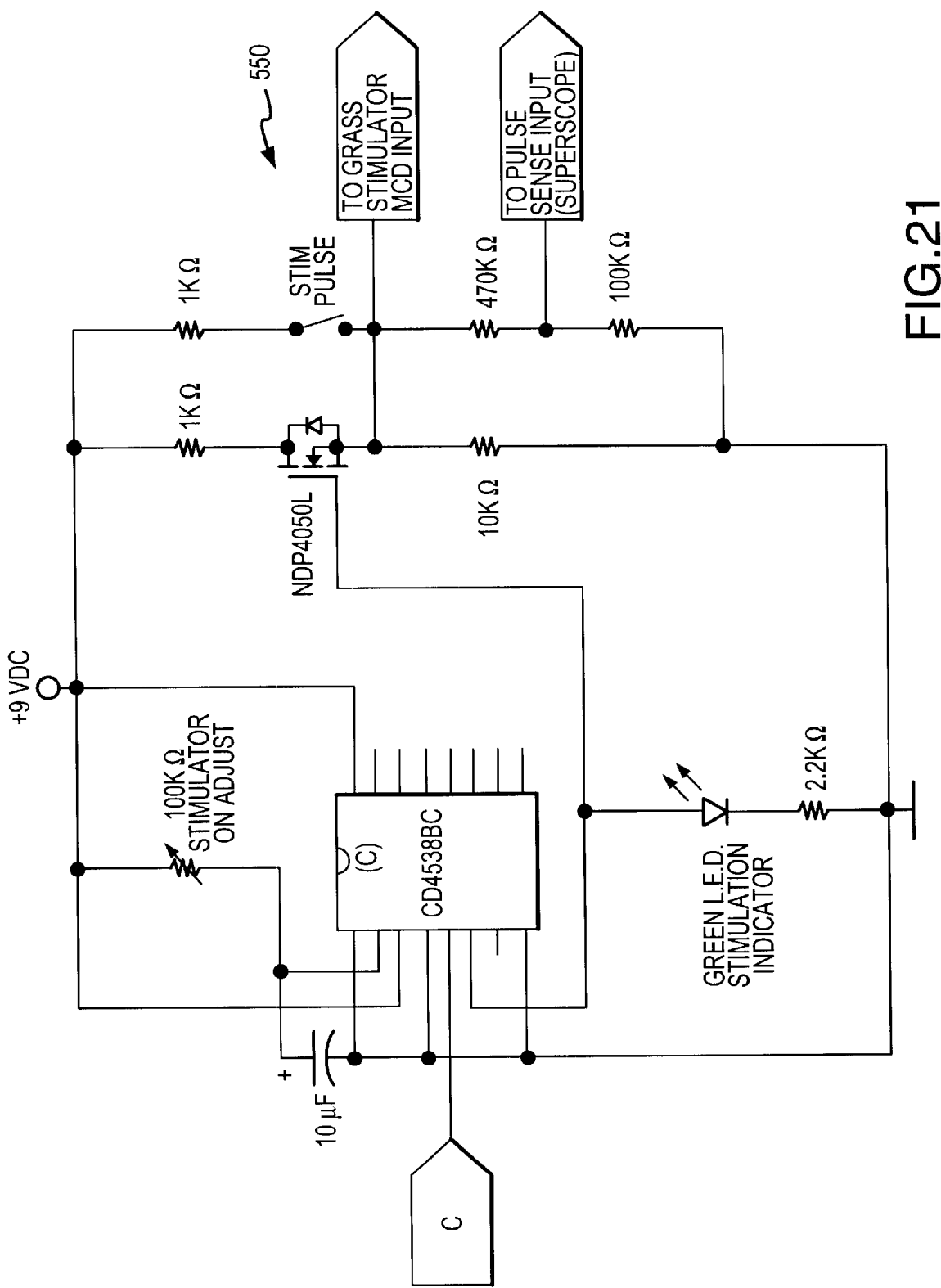
FIG. 21 illustrates a circuit diagram of a stimulator ON adjust module of the system of FIG. 13.

FIG. 21 illustrates a stimulator ON adjust module 550 that may be used to construct pulse train duration circuitry 418 of system 400. Module 550 functions to control how long the stimulator is "ON". In other words, module 550 determines how long the stimulator pulse train is delivered to the patient to stimulate the phrenic nerve.

Figure 22:
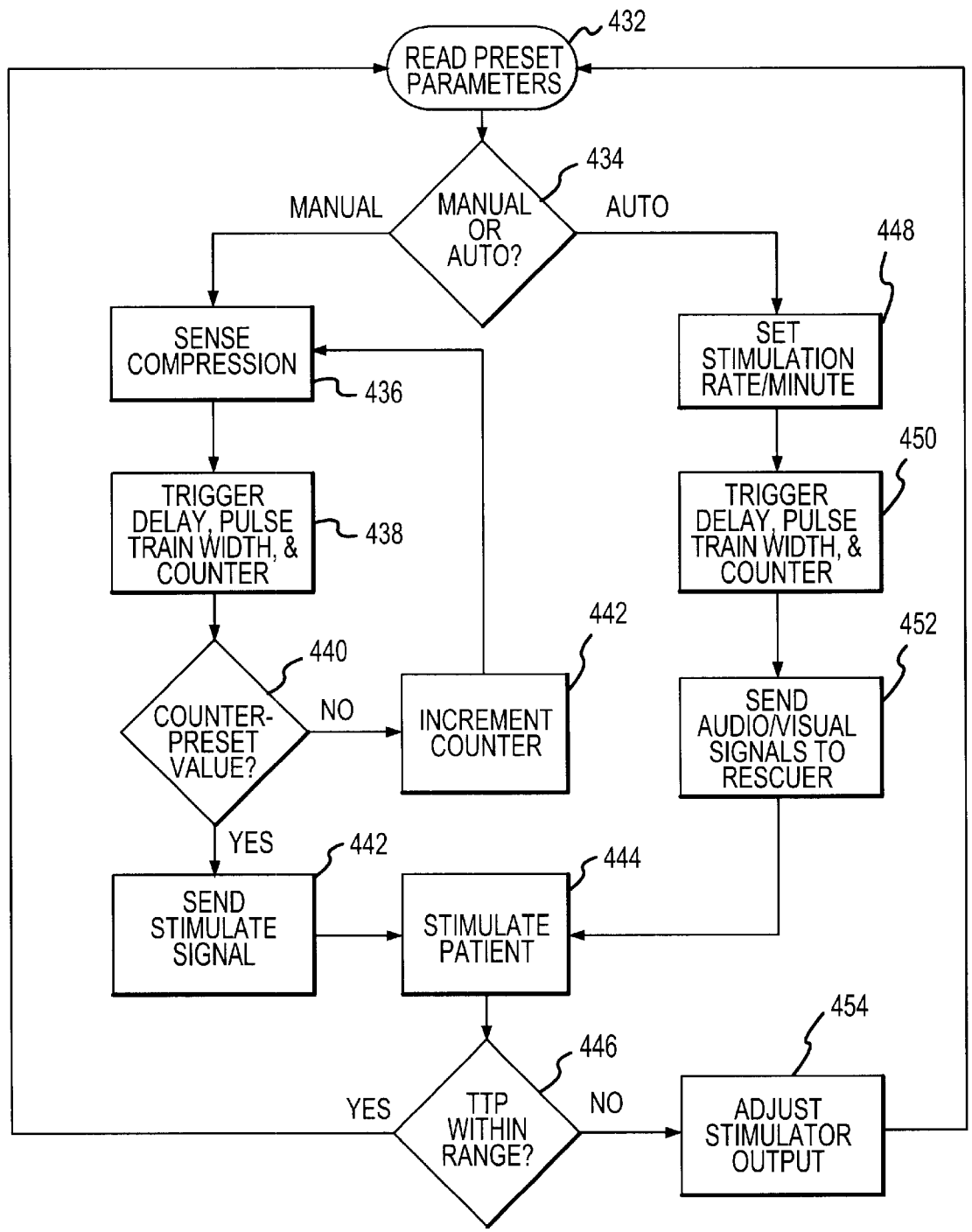
FIG. 22 is a flow chart illustrating methods for stimulating diaphragmatic compression in connection with chest compressions.

Referring now to FIG. 22, various methods for utilizing system 400 to treat a patient suffering from cardiac arrest will be described. As shown in step 432, the system is initialized by reading various preset parameters. The user then has the option to operate the system in manual or automatic mode as illustrated in step 434. If manual mode is selected, the system will be configured to stimulate diaphragmatic contraction based upon when the rescuer compresses the patient's chest. This process begins by sensing a chest compression as shown in step 436. After sensing chest compression, the production of the stimulating current is delayed for a certain preset time and is provided with a certain pulse train and pulse width as shown in step 438. Further, the chest compression is counted with a counter. The process then proceeds to step 440 where it is determined whether the counter has reached a preset value. If not, the process proceeds to step 442 where the counter is incremented and returns back to step 436 where the next chest compression is sensed. If the counter has reached the preset value, the stimulating signal is sent to the electrodes as shown in step 442 to stimulate the phrenic nerve as illustrated in step 444.

In step 446, the thoracic pressure is measured to determine whether it is within the range from about −15 to about −25 mm Hg. If the negative intrathoracic pressure is outside of this range, the stimulator output is adjusted as illustrated in step 454 and the process proceeds back to step 432. As previously described, system 400 may be used in non-CPR applications as well. In such situations, step 446 may be employed to ensure that the negative intrathoracic pressure within the patient remains within a desired range.

If the automatic mode is selected, the process proceeds to step 448 where the rescuer has the option of setting the stimulation rate, preferably in terms of stimulations per minute. System 400 is then configured to automatically stimulate the phrenic nerve using the electrodes. System 400 is further configured to produce the electrical signal with an appropriate pulse train duration and width as shown in step 450. To assist the user in performing chest compressions in a synchronized manner with diaphragmatic stimulation, the process includes step 452 where an appropriate audio-visual signal is produced to indicate to the rescuer when chest compressions should be performed. In another embodiment, the stimulator is turned on to stimulate the phrenic nerve at a given rate and the rescuer times the delivery of chest compressions based upon when the phrenic nerve is stimulated. Chest compressions are then delivered after each stimulation.

EXAMPLES

Various electrode mapping and electroventilation studies were performed to illustrate exemplary electrode placement strategies. The studies also focused on the type of electrical wave form and other characteristics of the stimulating signal, as well as the use of an inspiratory threshold valve to control the flow of respiratory gases to the lungs. It will be appreciated that the following examples are merely illustrative of certain electrode configurations, and that the invention is not intended to be limited only to the specific examples shown hereinafter.

The following examples evaluate the required energy to produce a given negative intrathoracic pressure. The examples were performed in 28–33 Kg female domestic pigs. A Grass S44 (Astro-Med, Inc.) square wave stimulator was modified to deliver either a monophasic or asymmetrical biphasic wave form at zero to 450 mA.

Example 1

Figure 23:
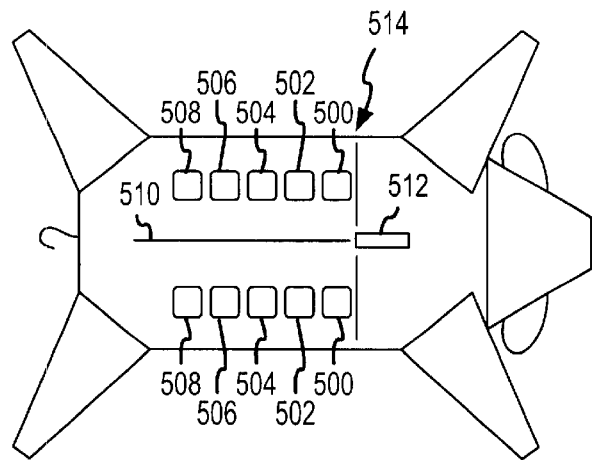
FIG. 23 is a schematic diagram of a transthoracic electrode map showing electrode placements for one example of the invention.

In this example, gel electrodes, having an outer dimension of 5 cm by 5 cm, were placed as shown in FIG. 23. An electrode control box (not shown) was developed to control the current flow between any electrode pair combinations. The electrodes were not removed or replaced during the study.

The invention utilized electrode pairs 500, 502, 504, 506 and 508. The medial edge of each electrode was placed 8 cm laterally from a midline 510 defined by the sternum 512, and 1 cm apart from each other superior to inferior from the xiphoid line 514. In an attempt to decrease the negative intrathoracic pressure during a stimulatory pulse stream, an impedance threshold valve was used to occlude the airway until a negative intrathoracic pressure of −22 cm $H_2O$ was reached. At this pressure, the valve was permitted to open, thereby allowing inspiratory air flow. The impedance threshold valve was similar to that described in U.S. Pat. Nos. 5,551,420 and 5,692,498, previously incorporated by reference.

The study was conducted in an anesthetized female domestic pig during normal profusion and sinus rhythm. Positive pressure ventilation was set at 12–16 breaths/minute and each stimulation pulse train occurred during the exhalation cycle of respiratory gas exchange. All studies measured the amount of negative intrathoracic pressure (mmHg) for each individual electrode pair or electrode pair combination. At 25 Hz, 110 volts, 250 microseconds pulse width, a 750 millisecond to 1 second monophasic pulse train was delivered during the exhalation cycle. The mean negative intrathoracic pressure values for each electrode pair are shown in Table 1.

TABLE 1

| Electrode Pair | Mean -ITP (mmHg) |
|---|---|
| 500 | 8.75 |
| 502 | 8.02 |
| 504 | 6.62 |
| 506 | 2.50 |
| 508 | 1.16 |

The data in Table 1 indicates that as transthoracic current is delivered to stimulate each hemisphere of the diaphragm, the electrode pair closest to the xiphoid line and thus superficially closer to the diaphragm, produced the greatest negative intrathoracic pressure deflection.

Example 2

The study of Example 2 was set up essentially identical to that of Example 1 except that the electrodes were stimulated in different paired combinations. Electride pair combinations produced a simulated electrode in which the surface area was increased according to the number of electrode pair combinations used. In Example 2, the electrical wave form patterns were changed to 30 Hz, 120 volts, 500 microseconds monophasic pulse width. The results of this study are shown in Table 2.

TABLE 2

| Electrode Pair Combination | Mean -ITP (mmHg) |
|---|---|
| 500/502 | 11.25 |
| 502/504 | 9.50 |
| 504/506 | 7.01 |
| 500/504 | 10.75 |
| 500/502/504 | 10.77 |
| 500/502/504/506 | 10.37 |

The data of Example 2 indicates that as transthoracic current is delivered between electrode pair combinations, the surface area of the simulated electrode disbursed the current which enabled a stronger contraction of the diaphragm and thus a greater negative intrathoracic pressure.

Example 3

The study of Example 3 utilized the 500/502/504 electrode pair combination at 50 Hz to 70 Hz, 90 volts, 500 microsecond monophasic pulse width. Blood gases were taken at the onset of each frequency change to monitor pH and determine if fatigue was apparent due to the increase in lactic acid and thus a decrease in pH. The results of this study are shown in Table 3.

TABLE 3

| Pulse Train Frequency (Hz) | Mean -ITP (mmHg) |
| --- | --- |
| 50 | 11.30 |
| 60 | 11.78 |
| 70 | 12.50 |

The data of Example 3 illustrates that an increase in frequency had a slight positive effect on increasing the magnitude of negative intrathoracic pressure. However, the pH became more acidic. This indicates that as the frequency increases, fatigue becomes more apparent and is reflected in a decrease in the magnitude of negative intrathoracic pressure and a decrease in pH due to lactic acid accumulation.

Example 4

In this study, the electrode pair combination 500/502 was used at 25 Hz to 70 Hz, 90 volts, 350 microseconds to 500 microseconds monophasic pulse width. Blood gases were taken at the onset of each frequency change to monitor pH. The results of this study as shown in Table 4.

TABLE 4

| Pulse Train Frequency (Hz) | Pulse Width ($\mu$s) | Mean -ITP (mmHg) |
| --- | --- | --- |
| 25 | 350 | 7.75 |
| 50 | 350 | 11.50 |
| 25 | 500 | 13.00 |
| 35 | 500 | 20.00 |
| 50 | 500 | 22.30 |
| 60 | 500 | 20.67 |
| 70 | 500 | 21.67 |

The data of Example 4 indicates that the optimal negative intrathoracic pressure target range of −15 mmHg to −20 mmHg may be achieved during transthoracic current flow between the 500/502 electrode pair combination. The data also indicates that by lowering the pulse stream frequency, the acidity of the pH was not as pronounced as in higher frequency. Moreover, the pulse width of the individual stimulation pulses appears to be optimal at 500 microseconds.

Example 5

This study utilized the 500/502 transthoracic electrode pair combination to evaluate wider stimulation pulse widths to determine if larger deflections in negative intrathoracic pressure would occur. Wave form parameters were adjusted at 500 Hz, 80 to 95volts, 500 microseconds to 5000 microseconds monophasic pulse width. Blood gases were taken at the onset of each frequency change to monitor pH. The results of this study are shown in Table 5.

TABLE 5

| Pulse Width ($\mu$s) | Voltage (Volts) | Mean -ITP (mmHg) |
| --- | --- | --- |
| 500 | 80 | 9.33 |
| 500 | 90 | 20.80 |
| 500 | 95 | 24.11 |
| 1000 | 90 | 23.33 |
| 3000 | 90 | 22.00 |
| 5000 | 90 | 20.00 |

The results of Example 5 indicate that as pulse width increased and/or voltage increased, a greater magnitude of negative intrathoracic pressure could be achieved. However, the tradeoff was an increase in acidosis when the pulse width, frequency, or voltage were increased.

Hence, with examples 1–5, fatigue appeared to be a significant obstacle. Accordingly, one aspect of the invention was to utilize a biphasic wave form to minimize the net charge transfer and thus minimize the charge accumulation on the electrode/tissue interface. An increase in charge accumulation on the electrode/tissue interfaces decreases net current flow between the stimulating electrodes, thereby reducing contraction of the diaphragm and reducing the desired deflection in negative intrathoracic pressure.

Figure 24A:
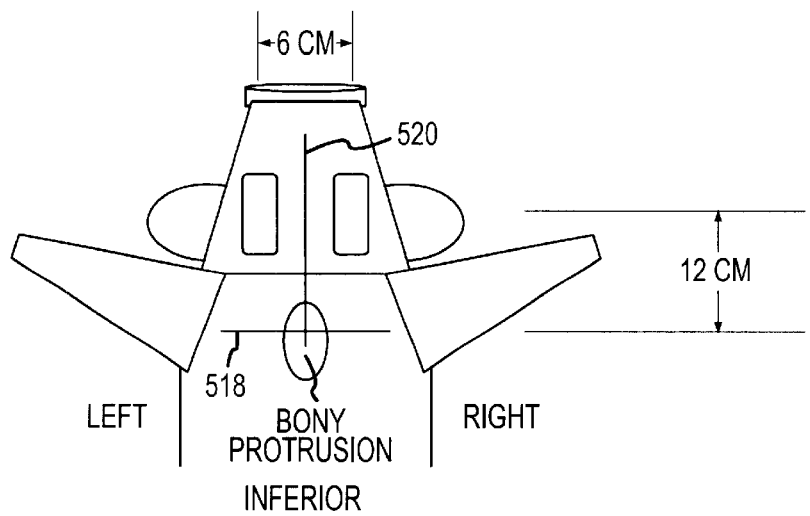
FIG. 24A is a schematic diagram of an electrode map showing anterior electrode positions for one example of the invention.

Accordingly, the remaining studies focus on stimulating the phrenic nerve in the cervical region of the spine. Anatomically, the phrenic nerve branches from the central nervous system between the cervical spine locations C3 through C5. The phrenic nerve descends inferior along the external jugular vein into the thoracic cavity. To stimulate the phrenic nerve in this region, gel electrodes having an outer perimeter of 4 cm by 9 cm were placed as shown in FIG. 24A (anterior locations) and FIG. 24B (posterior locations). As with examples 1–5, an electrode control box was used to control the current flow between any electrode pair combination and the electrodes were not removed or replaced during the study.

Figure 24B:
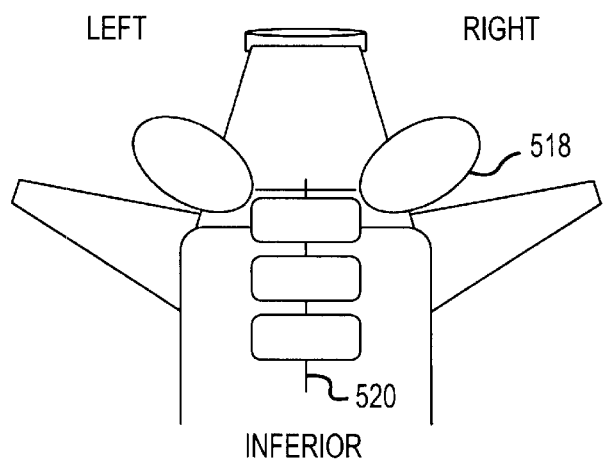
FIG. 24B is a schematic diagram of an electrode map showing posterior electrode positions for one example of the invention.

As shown in FIGS. 24A and 24B, ionic current flow was induced bilaterally anterior to posterior in the cervical region of the spine to initiate an action potential in the phrenic nerve causing the nerve to bilaterally fire and contract the diaphragm. In FIG. 24A, electrodes are placed centrally 12 cm from the bony protrusion reference line 518 and centrally 3 cm laterally from the central line 520. In FIG. 24B, the superior electrode is placed 3 cm from reference line 520 that is drawn between the bony indentation just behind the ears. The remaining electrodes are placed 1 cm apart descending in the inferior direction. Simulator electrodes were therefore created with 2 anterior electrodes and 3 posterior electrodes thus creating an anterior to posterior bipolar electrode configuration.

Example 6

With such a configuration, studies were conducted with anesthetized female domestic pigs under normal profusion and positive pressure ventilation. An asymmetrical biphasic wave form at a 500 microseconds pulse width and a 30 Hz pulse train frequency were fixed. The varying voltage parameter was adjusted between 60 and 150 volts pulsating direct current. The graphs of FIGS. 25–27 displayed the mean results of the studies.

Figure 25:
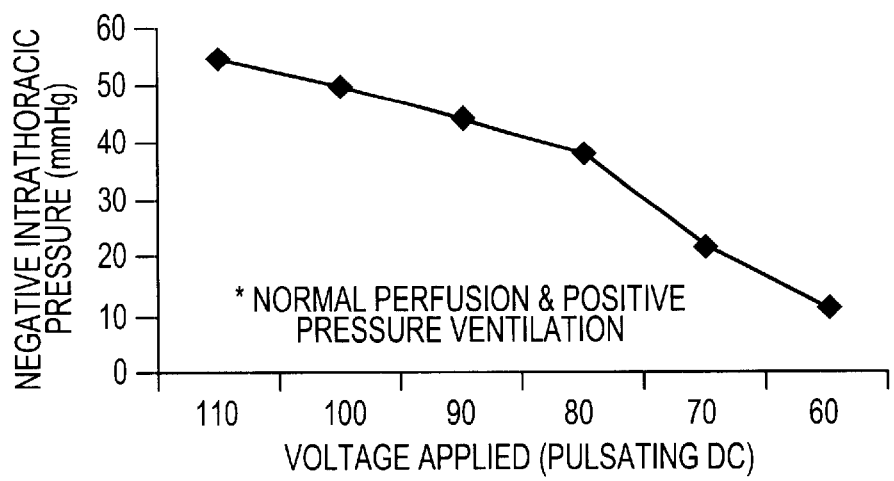
FIG. 25 is a graph illustrating the applied voltage to the electrodes of FIGS. 24A and 24B and the resulting negative intrathoracic pressure when using an impedance valve.

The graph of FIG. 25 displays the results of an inspiratory threshold valve assessment to determine the applicable voltage to obtain the target negative intrathoracic pressure between −15 mmHg and −20 mmHg. As with the previous studies, stimulation occurred during the exhalation cycle of positive pressure ventilation under normal profusion. As shown, less energy is required to achieve the target negative intrathoracic pressure utilizing this electrode configuration in conjunction with an asymmetrical biphasic form compared with other electrode configurations as in FIG. 23. Transthoracic electrode configurations required at least 90 volts pulsating DC compared to 60 to 70 volts pulsating DC with the cervical electrode configurations to produce the same deflection in negative intrathoracic pressure. Reproducibility with the cervical electrode configurations has been achieved in every study without failure.

Figure 26:
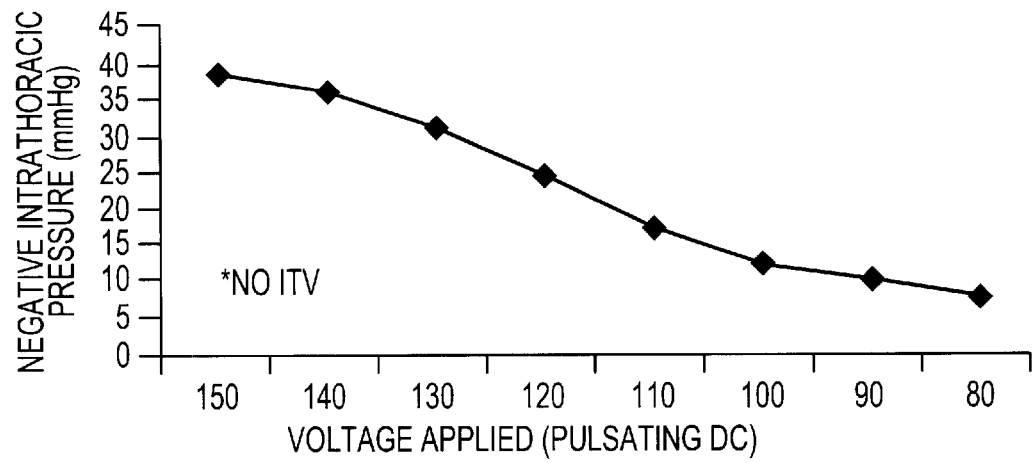
FIG. 26 is a graph illustrating the applied voltage to the electrodes of FIGS. 24A and 24B and the resulting negative intrathoracic pressure without the use of an impedance valve.

The graph of FIG. 26 illustrates the effects of cervical phrenic nerve stimulation and expiratory title volume. The graph of FIG. 26 depicts a representation of the amount of voltage required to produce the target negative intrathoracic pressure without the use of an impedance threshold valve. As shown, the amount of energy nearly doubles indicating that more energy is required to decrease the intrathoracic pressure negative without utilizing the impedance threshold valve.

Figure 27:
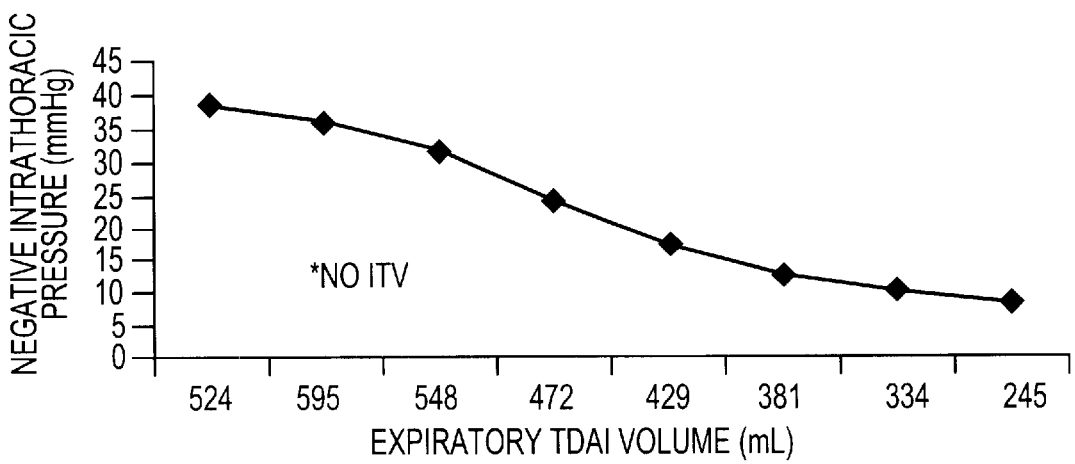
FIG. 27 is a graph illustrating the tidal volumes achieved at the corresponding negative intrathoracic pressures of the graph of FIG. 26.

The graph of FIG. 27 illustrates expiratory title volumes achieved at the corresponding negative intrathoracic pressure. As shown, cervical stimulation of the phrenic nerve generates sufficient gas exchange to sustain life by electroventilation.

The results of this study indicate that cervical electrode positioning utilized to initiate an action potential in the phrenic nerve are significantly easier to achieve when compared to transthoracic electrode configurations. Moreover, electroventilation has been easily reproduced with cervical phrenic stimulation.

Figure 28A:
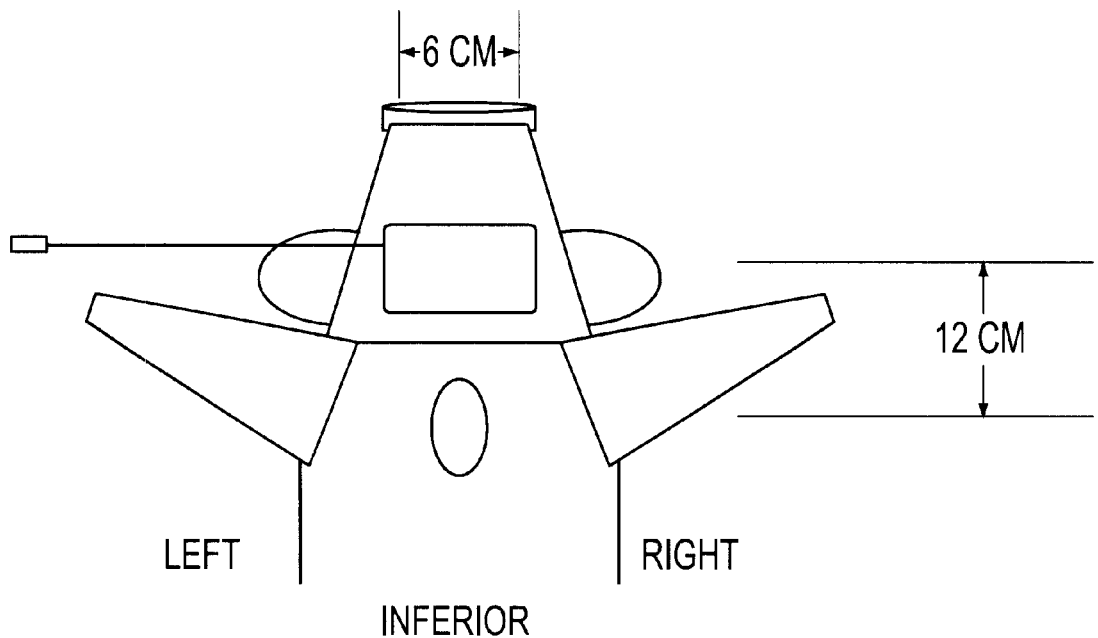
FIG. 28A is a schematic diagram of an alternative electrode map showing an anterior electrode position for one example of the invention.
Figure 28B:
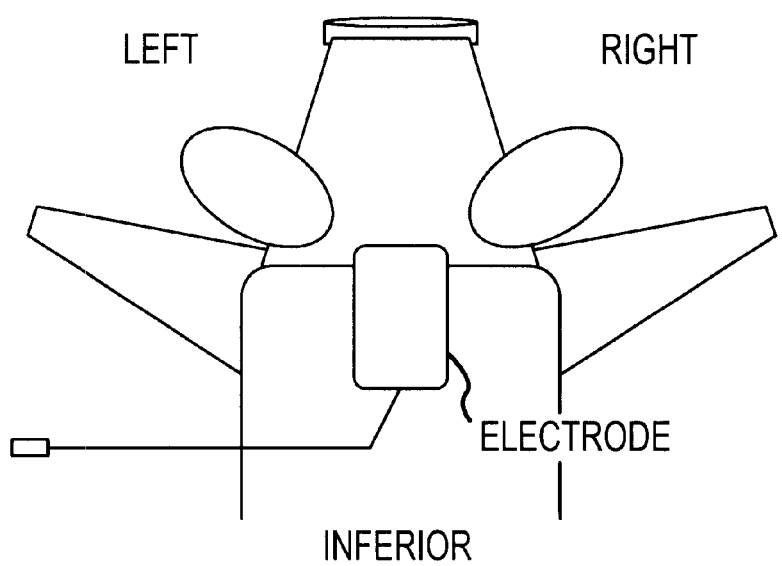
FIG. 28B is a schematic diagram of an electrode map showing a posterior electrode positions for one example of the invention.

FIGS. 28A and 28B illustrate another embodiment for single electrode placement. This electrode placement is similar to that of FIGS. 24A and 24B except that single electrodes are used for anterior and posterior placement.

Figure 29:
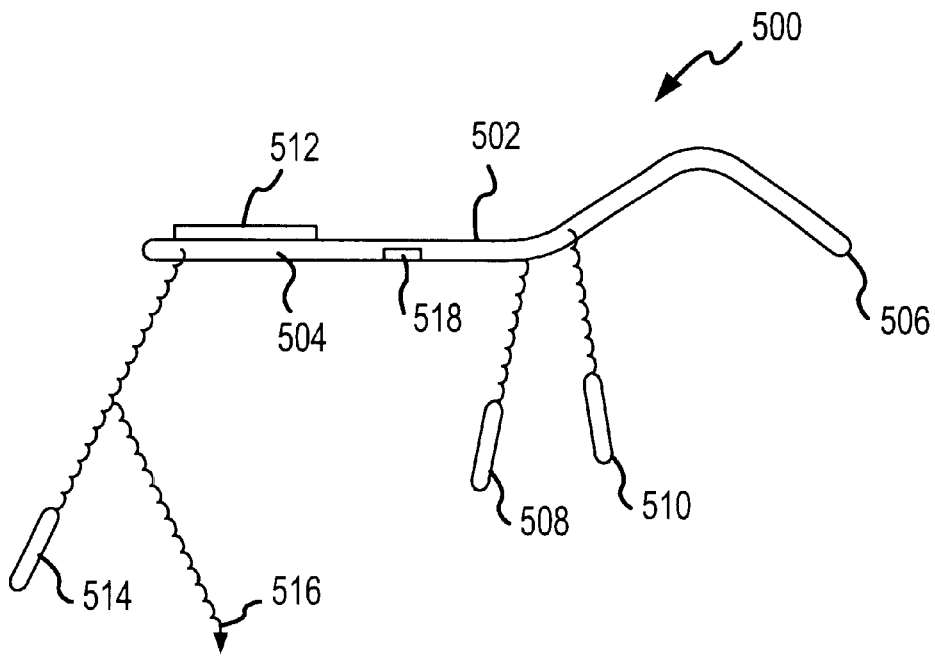
FIG. 29 is a schematic diagram of a stimulation device according to the invention.

FIG. 29 illustrates an embodiment of a stimulation device 500 that is constructed of a support body 502 comprising a back plate 504 and a neck support 506. Support body 502 may be constructed of essentially any type of rigid material, such as plastics, acrylics, and the like. In use, a patient is placed onto support body 502 such that the patient's back rests upon back plate 504. Further, neck support 506 is positioned against the patient's neck, forcing the patient's head backward to open the patient's airway. Conveniently, back plate 504 also provides support to the patient's back when performing CPR.

Coupled to support body 502 are a pair of electrodes 508 and 510 that may be used to electrically stimulate the phrenic nerve in a manner similar to that described with previous embodiments. Also coupled to support body 502 are a pair of electrodes 512 and 514 that may be used to provide a defibrillating shock. Ab electrical conductor 516 is provided to permit device 500 to be coupled to a defibrillator/stimulator to provide electrical current to the various electrodes. Optionally, an electrical port 518 may be provided to hold one or more electrical circuits that are to be used in controlling the various electrical shocks and/or stimulations supplied by the electrodes.

Figure 30:
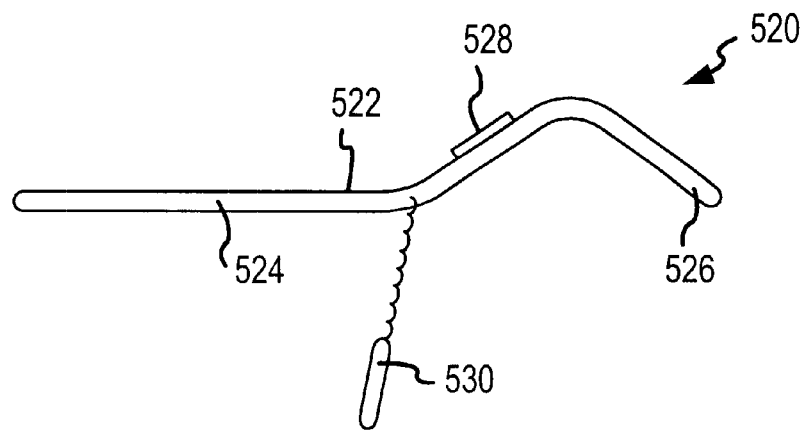
FIG. 30 is a schematic view of an alternative stimulation device according to the invention.

FIG. 30 illustrates an alternative embodiment of a stimulation device 520 that is constructed of a support body 522 comprising a back plate 524 and a neck support 526 in a manner similar to device 500. Device 520 includes a pair of electrodes 528 and 530. Electrode 528 is positioned so as to be adjacent the back of the patient's neck, while electrode 530 may be placed at the front of the patient's neck to stimulate the phrenic nerve. Although not shown, device 520 may include an electrical conductor to permit device 520 to be coupled to a stimulation unit.

Figure 31:
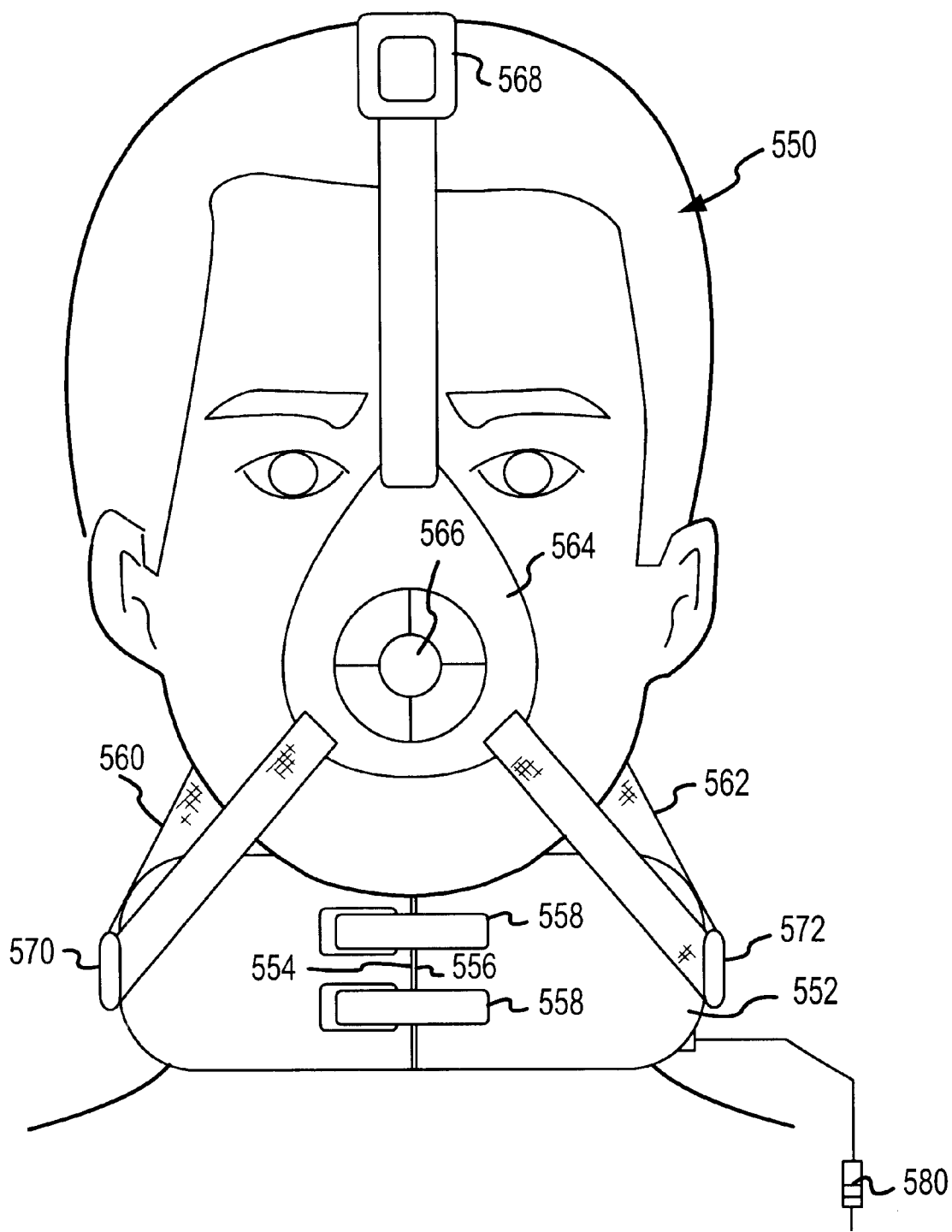
FIG. 31 is a schematic top view of a stimulation collar system that is attached to a patient according to the invention.
Figure 32:
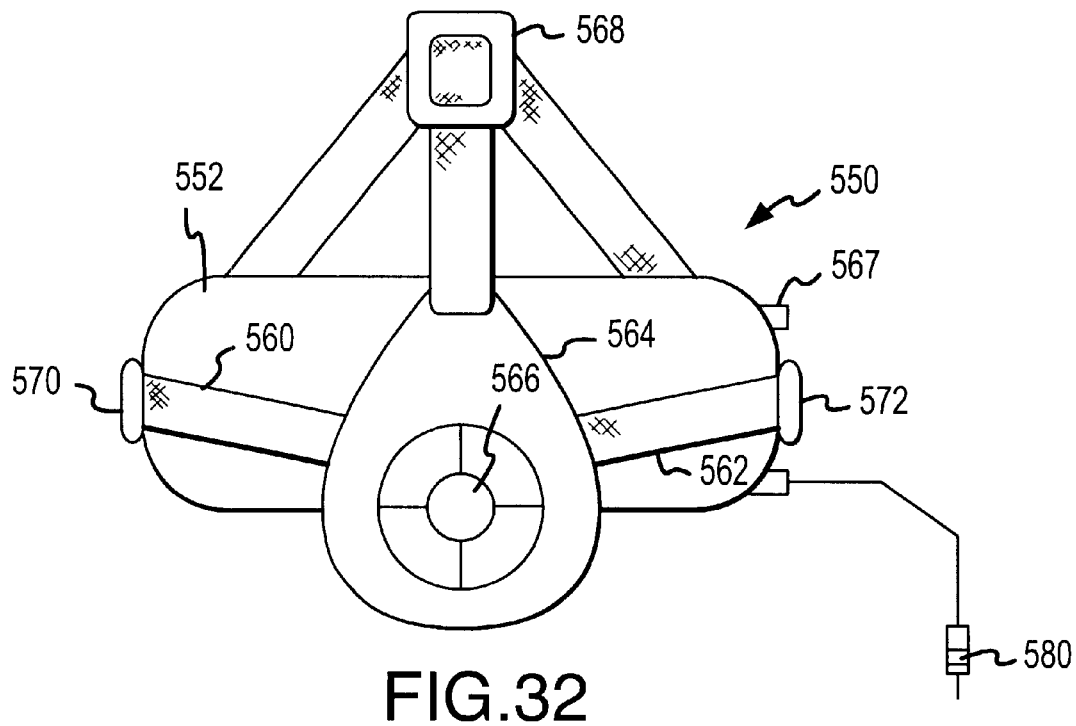
FIG. 32 is a top view of the system of FIG. 31 when removed from the patient.
Figure 33:
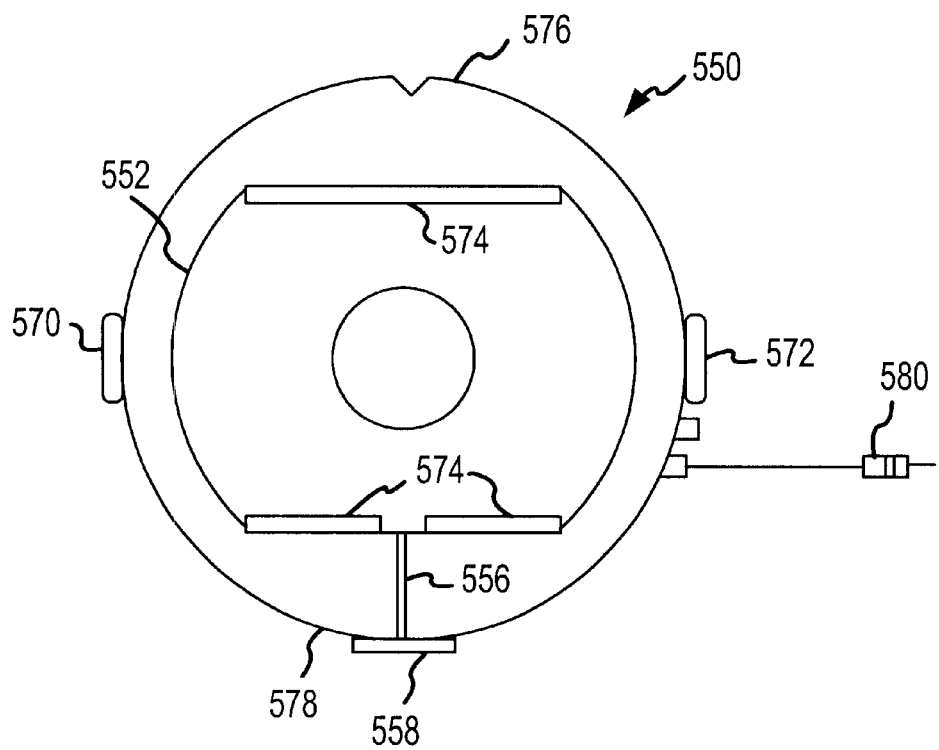
FIG. 33 is an end view of the system of FIG. 32.

As previously described in connection with FIG. 8A, a neck collar may be employed to stimulate the phrenic nerve. One embodiment of a neck collar system 550 is illustrated in FIGS. 31–33. System 550 comprises a neck collar 552 having two ends 554 and 556 that may be separated from each other to permit placement of collar 552 about the neck of a patient as shown in FIG. 31. Conveniently, one or more strips 558 of a hook and loop fastener material, such as Velcro fastener material, may be coupled to collar 552 to secure ends 554 and 556 adjacent each other after collar 552 has been placed about the neck. However, it will be appreciated that other types of connectors may be used.

Coupled to collar 552 by elastic straps 560 and 562 is a face mask 564 that may include an impedance threshold valve system 566 that is configured similar to other embodiments described herein. To couple mask 564 to the patient's face, straps 560 and 562 are positioned on top of the patient's head and extend downward to the patient's neck as shown in FIG. 31. Once straps 560 and 562 are positioned, collar 552 is positioned around the patient's neck and secured into position.

Once collar 552 is secured in place, collar 552 may be inflated using an inflation port 567 to maintain adequate contact between the stimulation electrodes and the surface of the patient's skin. Face mask 564 may also be adjusted to the proper position by the use of an adjustable head buckle 568 and the use of fasteners 570 and 572 that permit straps 560 and 562, respectively, to slide relative to collar 552.

Disposed within collar 552 are stimulating electrodes 574 to stimulate the phrenic nerve to contract. Electrodes 574 are placed on both a posterior side 576 and an anterior side 578 to facilitate phrenic nerve stimulation in a manner similar to that described in connection with other embodiments. An electrode connector 580 is provided to permit electrodes 574 to be coupled to a stimulation unit.

Figure 34:
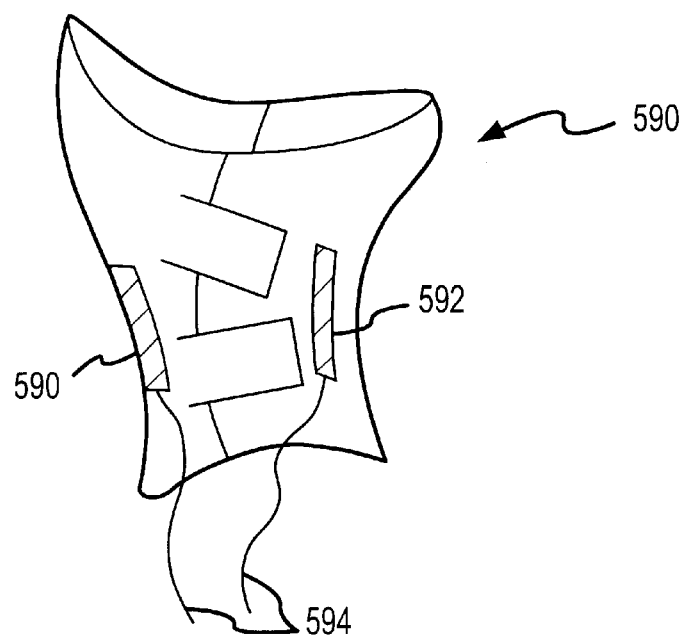
FIG. 34 is a side view of another embodiment of a neck collar having stimulating electrodes according to the invention.

FIG. 34 illustrates another embodiment of a neck collar 590 that may be used to stabilize the neck and open the patient's airway. Collar 590 further includes stimulation electrodes 590 and 592 for stimulating the phrenic nerve in a manner similar to that described in connection with other embodiments. Leads 594 are coupled to electrodes 590 and 592 to permit the electrodes to be coupled to a stimulation unit. Conveniently, collar 590 may be constructed in two halves to permit each attachment and removal. Attachment straps 596 may be used to hold the two halves together. As previously described, the techniques of the invention may find use in treating hypovolemic or hemorrhagic shock. Trauma induced hypovolemic shock can be a principal cause of death in humans. Unfortunately, the chances for survival after trauma and subsequent blood volume loss are not favorable in environments where rapid rescue attempts and blood volume replenishment are not immediately available. To aid in improving survival after excessive blood volume loss and prior to blood volume replenishment, the invention provides techniques and equipment to sustain adequate hemodynamic parameters for a prolonged period of time until volume replenishment can occur.

Such techniques may employ the use of two components: a system to regulate airflow to the patient's lungs, and a lifting device to actively lift the patient's chest. For example, the invention may utilize an impedance threshold valve, as described generally in the preceding text and in U.S. Pat. No. 5,692,498, previously incorporated by reference. Further, to lift the chest, the invention may utilize an active chest compression/decompression device, such as those that are commercially available from Ambu International and described generally in U.S. Pat. No. 5,645,552, incorporated herein by reference. Alternatively, the invention may utilize any device capable of lifting the chest including, for example, suction cups, adhesives, and the like. Further such devices may be hand held, manually operated, or automated (such as a piston having a suction cup at a bottom end). Further, as previously described, phrenic nerve stimulation may be used to decrease thoracic pressures. This may be used alone or in combination with active lifting of the chest.

During hypovolemic shock, systolic blood pressures can often drop to extremely low levels resulting in minimal blood perfusion and tissue ischemia. To improve hemodynamics during hypovolemic and other types of shock, one method controls incoming airflow and actively lifts the chest to decrease intrathoracic pressure and increase venous return to the right chambers of the heart from the peripheral venous vasculature. For example, the sternum and the anterior rib cage may be actively lifted. The increased venous blood volume return thus increases cardiac chamber filling volumes and greatly improves hemodynamic parameters in patients with a functional beating heart.

Figure 35:
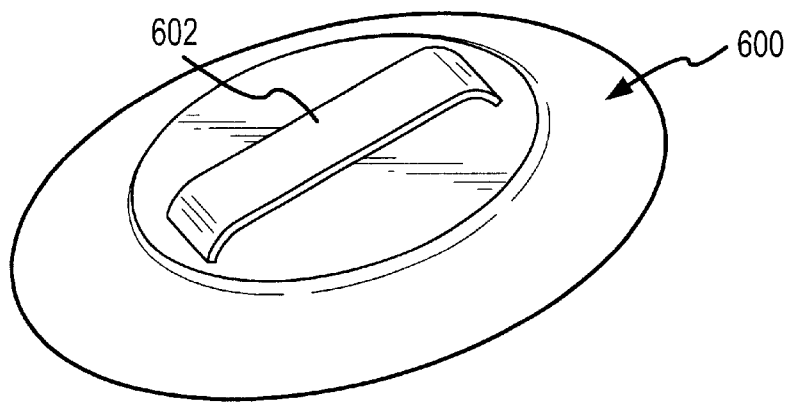
FIG. 35 is a top perspective view of a lifting device that may be used when treating a patient suffering from hypovolemic or hemorrhagic shock according to the invention.
Figure 36:
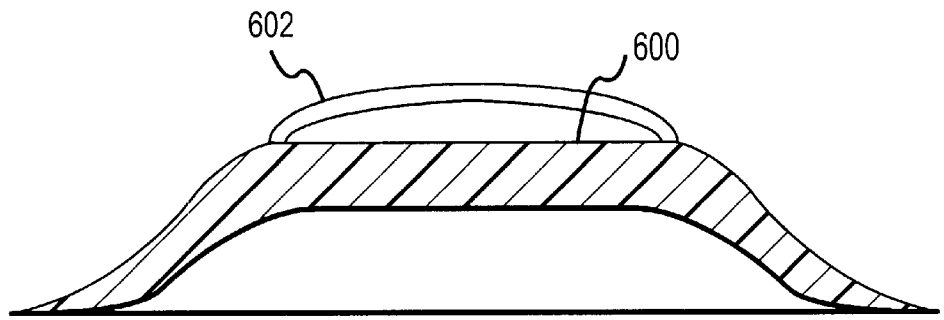
FIG. 36 is a cross sectional side view of the device of FIG. 35.

In one specific embodiment, the method utilizes a suction cup device 600 as shown in FIGS. 35 and 36 that attaches to the patient's chest. The suction cup device 600 creates a vacuum seal with the patient's chest allowing the rescuer to lift up on a handle 602 and raise the patient's thoracic cavity. Raising the thoracic cavity lowers the intrathoracic pressure and increases venous return from the peripheral vasculature to the beating heart. Repeatedly raising and lowering the patient's thoracic cavity creates a vacuum pumping mechanism that enhances central venous return and improves overall cardiopulmonary circulation. In cases where the patient is essentially lacking a blood pressure, the patient's chest may be actively lifted without also compressing the chest. However, if the patient has a moderate blood pressure, the patient's chest may optionally be compressed in an alternating manner with chest decompressions.

The volume of venous return is further enhanced by lowering the intrathoracic pressure more negatively with the use of an impedance threshold valve. The impedance threshold valve functions to increase central venous return by impeding airflow into a patient's lungs during chest elevation, thus enhancing the extent and duration of negative intrathoracic pressure. The impedance threshold valve is connected to the patient's airway through use of an external face mask, an internal endotracheal tube inserted into the patient's trachea during intubation, or the like. Merely by way of example, when treating hemorrhagic shock, the patient's chest may be actively lifted in the range from about 20 to about 60 times per minute. Further, the impedance valve may be set to prevent air flow to the lungs until reaching a negative intrathoracic pressure that is in the range from about −5 to about −30 cmH$_2$O. Periodically, the patient may also be ventilated.

The enhanced extent and duration of negative intrathoracic pressure during chest elevation and the impedance of inspiratory airflow promotes venous blood flow into the heart and lungs from the peripheral venous vasculature. Increased venous return aids the beating heart in circulating more oxygenated blood to the vital organs under hypovolemic shock conditions. Therefore, the increase in systemic circulatory flow and systolic blood pressure produced by this method significantly reduces ischemia in vital organ or peripheral tissue vasculature. The increase in tissue perfusion can be sustained for a prolonged period of time utilizing this method and devices prior to volume replenishment and further rescue attempts.

The invention has now been described in detail. However, it will be appreciated that certain changes and modifications may be made. Therefore, the scope and content of this invention are not limited by the foregoing description. Rather, the scope and content are to be defined by the following claims.

What is claimed is:

1. A method for treating a patient suffering from shock, the method comprising:

coupling a flow control system to the patient's airway, wherein the flow control system is configured to limit or prevent the flow of respiratory gases into the patient's lungs for at least some time; and permitting the patient to gasp or inspire air, with the flow control system limiting or preventing the flow of respiratory gases into the lungs for at least some time during the gasp or breath to decrease the patient's intrathoracic pressure and to increase venous return to the right chambers of the heart from the peripheral venous vasculature to improve hemodynamic parameters of the patient and thereby treat the patient for shock.

2. A method as in claim 1, wherein the flow control system comprises an impedance threshold valve that is configured to prevent respiratory gases from flowing to the lungs until a threshold actuating pressure is achieved.

3. A method as in claim 2, wherein the impedance threshold valve is configured to open when the negative intrathoracic pressure is in the range from about −5 cm H2O to about −30 cm H2O.

4. A method as in claim 1, wherein the patient is suffering from a type of shock selected from a group consisting of hypovolemic shock, hemorrhagic shock or cardiogenic shock.

5. A method as in claim 1, further comprising stimulating the patient to cause the patient to gasp.

* * * * *

UNITED STATES PATENT AND TRADEMARK OFFICE
CERTIFICATE OF CORRECTION

PATENT NO. : 6,587,726 B2  Page 1 of 1
DATED : July 1, 2003
INVENTOR(S) : Keith G. Lurie et al.

It is certified that error appears in the above-identified patent and that said Letters Patent is hereby corrected as shown below:

Title page, Item [54] and Column 1, lines 1-3,
Title should read -- METHODS FOR TREATING A PATIENT SUFFERING FROM SHOCK --

Title page,
Item [75], Inventors, should read:
-- [75] Inventors: Keith G. Lurie
                        Todd M. Zielinski --

Signed and Sealed this

Ninth Day of December, 2003

JAMES E. ROGAN
*Director of the United States Patent and Trademark Office*